United States Patent [19]
Schwartz et al.

[11] Patent Number: 5,157,031
[45] Date of Patent: Oct. 20, 1992

[54] METHOD FOR PROPHYLAXIS OF OBESITY

[75] Inventors: Arthur G. Schwartz, Philadelphia; Marvin L. Lewbart, Media, both of Pa.

[73] Assignee: Research Corporation Technologies, Inc., Tuscon, Ariz.

[21] Appl. No.: 326,355

[22] Filed: Mar. 21, 1989

Related U.S. Application Data

[63] Continuation of Ser. No. 867,112, May 21, 1986, abandoned, which is a continuation-in-part of Ser. No. 519,550, Aug. 2, 1983, abandoned.

[51] Int. Cl.$^5$ .................. A61K 31/565; C07J 1/00
[52] U.S. Cl. .................. 514/177; 552/536; 552/624; 552/650; 552/651; 552/652; 552/505; 552/522; 552/516
[58] Field of Search .................. 260/397.7; 514/177, 514/909

[56] References Cited

U.S. PATENT DOCUMENTS 4,897,390  1/1990  Ruhe et al. ..................... 514/177

FOREIGN PATENT DOCUMENTS 133995  3/1985  European Pat. Off. .

OTHER PUBLICATIONS

Fels Research Institute pp. 32–33 (1980).

Primary Examiner—Nicholas S. Rizzo
Attorney, Agent, or Firm—Scully, Scott, Murphy & Presser

[57] ABSTRACT

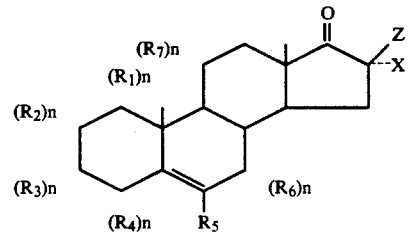

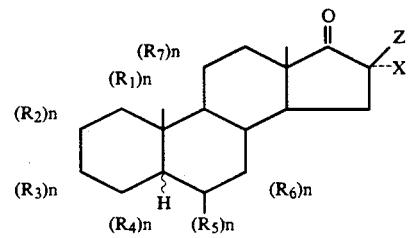

useful as anti-cancer, anti-obesity, anti-hyperglycemic, anti-autoimmune and anti-hypercholesterolemic agent.

19 Claims, No Drawings

METHOD FOR PROPHYLAXIS OF OBESITY

This invention described herein was made in the course of work under a grant or award sponsored in part by the National Institutes of Health.

This is a continuation of copending application Ser. No. 867,112, abandoned filed on May 21, 1986 which is a continuation-in-part of U.S. patent application Ser. No. 519,550, filed on Aug. 2, 1983, now abandoned.

BACKGROUND OF THE INVENTION

This invention relates to novel steroids and more particularly to androsterone derivatives useful as anti-cancer, anti-obesity, anti-diabetic and hypolipidemic agents.

Dehydroepiandrosterone (DHEA) and DHEA-sulfate are major adrenal secretory products in humans. The plasma concentration of DHEA-sulfate, which, next to cholesterol, is the most abundant steroid in humans, undergoes the most marked age-related decline of any known steroid.

Although DHEA-sulfate is the main precursor of placental estrogen and may be converted into active androgens in peripheral tissue, there is no obvious biological role for either DHEA or DHEA-sulfate in the normal individual. Several retrospective and prospective studies suggest that women with sub-normal levels of these steroids may be predisposed to develop breast cancer. For example, see Brownsey, et al., "Plasma dehydroepiandrosterone sulfate levels in patients with benign and malignant breast disease, Eur. J. Cancer, 8, 131–137 (1972); Bulbrook, et al., "Relation between urinary androgen and corticoid excretion and subsequent breast cancer, "Lancet, 2, 395–398 (1971); Rose, et al., "Plasma dehydroepiandrosterone sulfate, androstenedione and cortisol, and urinary free cortisol excretion in breast cancer, "Eur. J. Cancer, 13, 43–47 (1977); Wang, et al., "Studies of the sulfate esters of dehydroepiandorsterone and androsterone in the blood of women with breast cancer," Eur. J. Cancer, 10, 477–482 (1974); and zumoff, et al., "Abnormal 24-hr mean plasma concentrations of dehydroisoandrosterone and dehydroisoandrosterone sulfate in women with primary operable breast cancer," Cancer Research, 41, 3360–3363, September 1981.

It has also been established that DHEA is a potent non-competitive inhibitor of mammalian glucose-6-phosphate dehydrogenase (G6PDH). For example, see Oertel, et al., "The effects of steroids on glucose-6-phosphate dehydrogenase," J. Steroid Biochem., 3, 493–496 (1972) and Marks, et al., "Inhibition of mammalian glucose-6-phosphate dehydrogenase by steroids," Proc. Nat'l Acad. Sci, U.S.A., 46, 477–452 (1960). Moreover, Yen, et al., "Prevention of obesity in A$^{vy}$/a mice by dehydroepiandrosterone," Lipids, 12, 409–413 (1977), reported that long-term administration of DHEA to VY-A$^{vy}$/a mice prevented the development of obesity without suppressing appetite.

Furthermore, it is also known that the long-term treatment of C3H mice with DHEA, in addition to reducing weight gain without suppressing appetite, markedly inhibits spontaneous breast cancer development and may delay the rate of aging. It has been observed that DHEA antagonizes the capacity of the tumor promoter, 12-0-tetradecanoylphorbol13-acetate, to stimulate $^3$H-thymidine incorporation in mouse epidermis and in a cultured rat kidney epithelial cell line. See, Schwartz, "Inhibition of spontaneous breast cancer formation in female C3H-A$^{vy}$/a mice by long-term treatment with dehydroepiandrosterone, Cancer Res., 39, 1129–1132 (1979); and Schwartz, et al., "Dehydroepiandrosterone: and anti-obesity and anti-carcinogenic agent," Nut. Cancer 3, 46–53 (1981).

Ben-David, et al., "Anti-hypercholesterolemic effect of dehydroepiandrosterone in rats," Proc. Soc. Expt. Biol. Med., 125, 1136–1140 (1967) have observed that DHEA treatment has an anti-hypercholesterolemic effect in mice, while Coleman, et al. (Diabetes 31, 830, 1982) report that administration of DHEA produces a marked hypoglycemic effect in C57BL/KsJ-db/db mice. The latter authors suggest that the therapeutic effect of DHEA might result from its metabolism to estrogens.

It is further known that DHEA and 16-bromo-epiandrosterone are inhibitors of Epstein-Barr virus-induced transformation of human lymphocytes and that 16-bromo-epiandrosterone is a more potent inhibitor of mammalian G6PDH than DHEA. See, Schwartz, et al. Carcinogensis, Vol. 2 No. 7, 683–686 (1981).

While DHEA has been found effective in the afore-described manners, there is however, evidence of an estrogenic effect after prolonged administration. DHEA is not an estrogen per se but is well known to be convertible into estrogens. In addition, the therapeutic dose of DHEA is rather high. It would therefore be highly desirable to provide steroids, which while having the same afore-described advantage of DHEA are more potent and do not produce an estrogenic effect.

SUMMARY OF THE INVENTION

Accordingly, the present invention provides novel steroids.

The steroids of the present invention exhibit significant and desirable pharmacological properties, and are particularly useful as cancer preventive agents.

The above-identified steroids are additionally useful as anti-obesity agents, anti-hyperglycemic agents, anti-aging agents, and anti-hypercholesterolemic agents.

This invention further provides steroids useful as anti-cancer, anti-obesity, anti-hyperglycemic, anti-aging, and anti-hypercholesterolemic agents, which do not evidence estrogenic effects.

The present invention also provides a process for the treatment and/or prevention of cancer, obesity, aging, diabetes, and hyperlipidemia.

The present invention also provides steroids useful for the treatment and/or prevention of autoimmune diseases, such as Coomb's positive hemolytic anemia and lupus erythematosus.

The present invention provides novel steroids of the general formula:

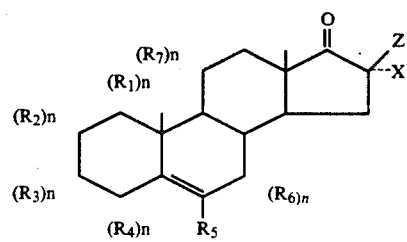

wherein $R_1$, $R_2$, $R_4$, $R_5$, $R_6$ and $R_7$ are each independently hydrogen or lower alkyl;

$R_3$ is hydrogen;

X is halogen, hydroxy, hydrogen, lower alkyl, lower alkoxy;

Z is lower alkyl or hydrogen; and n is 1 or 2; with the proviso that at least one of X and Z is other than hydrogen.

The present invention is also directed to compounds of the formula:

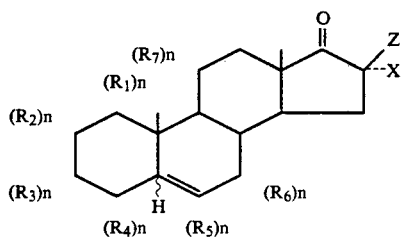

wherein $R_1$, $R_2$, $R_4$, $R_5$, $R_6$, and $R_7$ are each independently hydrogen or lower alkyl;

$R_3$ is hydrogen;

X is halogen, hydroxy, hydrogen, lower alkyl, lower alkoxy;

Z is lower alkyl or hydrogen; and n is 1 or 2;

with the proviso that at least one of X and Z is other than hydrogen.

The preferred compounds of Formula II are the α-androstan-17-one derivatives.

The present invention provides processes for the prophylaxis of cancer, obesity, aging, diabetes, and hyperlipidemia and autoimmune diseases, such as lupus erythematosus or Coomb's positive hemolytic anemia comprising administering to a host, e.g., mammals, a therapeutically effective amount of the present new steroids.

In accordance with the present invention, it has been surprisingly discovered that steroids having a certain structure, described hereinabove and hereinafter in more detail, are characterized with significant pharmacological properties without toxic or undesirable estrogenic effects. That is, it has been quite unexpectedly discovered that the steroids of the present invention are useful as cancer preventive, anti-obesity, anti-diabetic, anti-aging, anti-autoimmune and anti-hypercholesterolemic agents, but unlike DHEA are more potent and exhibit very little or no estrogenic effect. Furthermore, unlike DHEA compounds of the present invention do not induce liver enlargement and increased catalase activity.

In the present invention, the alkyl groups are preferably lower alkyl, which may be straight or branched chain, and which contain up to 5 carbon atoms. Examples include methyl, ethyl, propyl, isopropyl, butyl, isobutyl, pentyl, amyl and the like. The most preferred alkyl group is methyl.

The halo atoms are preferably Br, F or Cl, especially F.

Additional variations in the structural formula representing the instant compounds can be effected without significantly altering the therapeutic properties. For example, the alkyl moieties can be substituted by one or more of a variety of substituents, such as hydroxy, halogen, alkoxy and the like.

The various substituents are designated as being in the α-position by means of a broken line (---) joining the substituent to the steroid nucleus. The substituents are designated as being in the β-position by means of a solid line (—) joining the substituent to the steroid nucleus. In those cases in which the substituents may be either in the α- or β-positions, the substituents are indicated as being joined to the steroid nucleus by a broken line and a solid line placed side to side. Furthermore, in accordance with I.U.P.A.C. nomenclature, the carbon atoms of the steroids of the present invention are numbered as follows and the steroids have the designated I.U.P.A.C. stereochemistry:

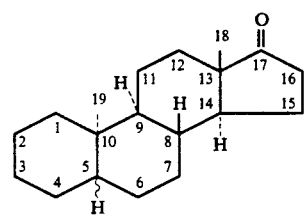

Specific illustrative compounds in accordance with the present invention include:

16α-hydroxy-5-androsten-17-one;
16α-fluoro-5-androsten-17-one;
16α-fluoro-16β-methyl-5-androsten-17-one;
16α-methyl-5-androsten-17-one;
16β-methyl-5-androsten-17-one;
16α-hydroxy-5α-androstan-17-one;
16α-fluoro-5α-androstan-17-one;
16α-fluoro-16β-methyl-5α-androstan-17-one;
16α-methyl-5α-androstan-17-one;
16β-methyl-5α-androstan-17-one.

The steroids of the present invention may be prepared in accordance with conventional organic syntheses. The following procedures are illustrative of some procedures which may be utilized to prepare the steroids included herein.

For example, the steroids of the present invention can be prepared from steroids which are known or are readily available, such as dehydroepiandrosterone (DHEA), by methods of alkylation, halogenation, hydroxylation or substitution reactions known in the art. For those final products which contain both an alkyl group and a halogen or hydroxy group the various substituents may be added to the steroid in any order, but it is preferred that the alkylation step precedes the halogenation, hydroxylation or substitution step.

ALKYLATION

CARBON-1 ALKYLATION

A representative procedure for alkylation at carbon-1 and specifically the synthesis of 1α-methyl-desoxy DHEA is given in Scheme I.

SCHEME 1

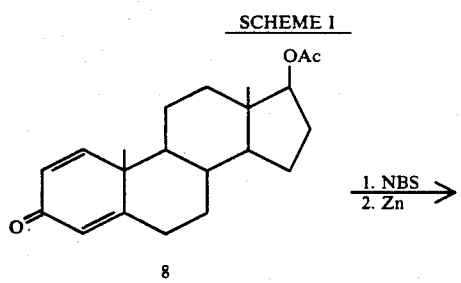

8

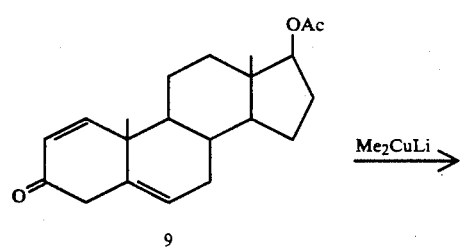

9

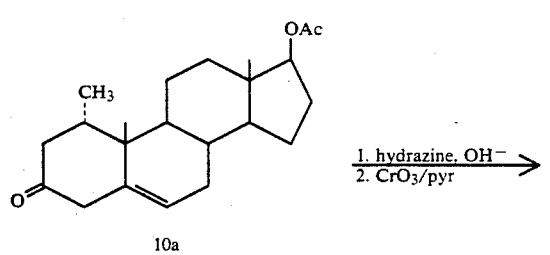

10a

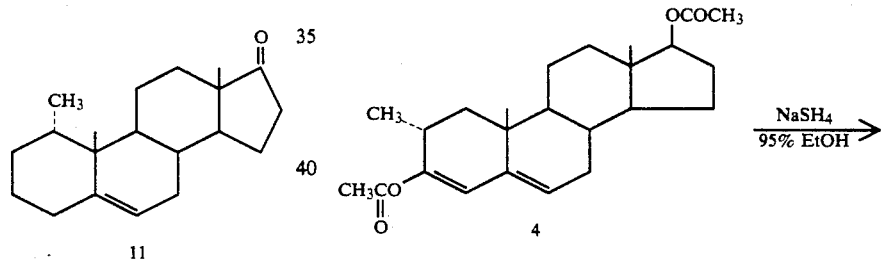

11

Allylic bromination (e.g. with N-bromosuccinimide (NBS) of 17β-acetoxyandrosta-1,4-dien-3-one 8 followed by treatment with zinc affords the non-conjugated enone 9. Alkylation with organometalic alkylating agents, such as lithiodimethyl cuprate, provides the 1α-methyl ketone 10a. At this stage the keto group of 10a may be converted to methylene by a Wolff-Kishner reduction or the Huang-Minlon modification thereof. These vigorous reaction conditions result in hydrolysis of the resulting carbon-17 acetate, thereby yielding the hydroxy desoxy derivative, 17β-hydroxy-1-α-methyl-5-androstene. The desoxy derivative can be converted to the final product by oxidation with an oxidizing agent, such as chromium trioxide in pyridine (11).

CARBON-2-ALKYLATION

The following procedures are illustrative for alkylation at carbon-2 and are figuratively illustrated in Scheme 2 below.

SCHEME 2

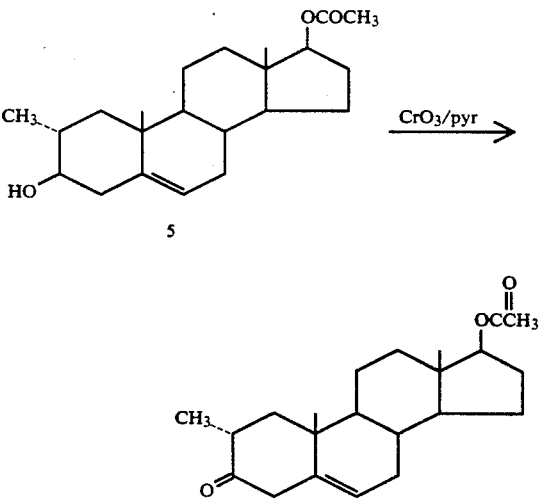

-continued
SCHEME 2

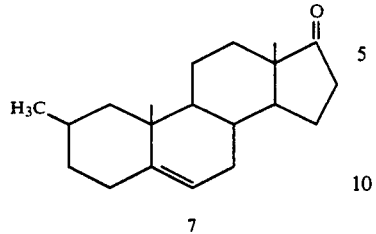

Alkylation of testosterone (I) with an alkylating agent, such as methyl iodide, in the presence of a strong base, such as t-BuOK, sodium t-pentoxide, lithium disopropyl amide (LDA), $NaNH_2$, $Et_2Ni$, n-butyl lithium and the like gives a mixture of the 2α- and 2β-alkyl 17-β-hydroxy-4-androsten-3-one (2 and 3). Treatment of the mixture with a strong base, such as sodium methoxide in methanol, epimerizes the 2β-axial alkyl to the 2α-equitorial configuration. (2) Acetylation of 2 with an acetylating agent, such as acetic anhydride ($Ac_2O$) and p-toluenesulfonic acid (p-TSA) in toluene affords the 2-αalkyl-3,5-androstadien-3,17-diacetate. (4). Treatment of the diacetate (4) with sodium borohydride in 95% ethanol yields the 2α-methyl-3βhydroxy-5-androsten-17-acetate (5). Oxidation of 5 with an oxidizing agent, e.g., Jones reagent, chromic oxide in pyridine, and the like, affords the ketone (6). The keto group of 6 is converted to a methylene group via the Wolff-Kishner reduction or the Huang-Minlon modification thereof. Hydrolysis of this product followed by oxidation with an oxidizing agent, such as chromium trioxide, gives the corresponding 17-ketone (7).

Alternatively, 7 can be formed from 5 by a different route, as shown in Scheme 2A. 5 is reacted with 0-phenylenephosphorochloridite (O-PPC) to produce the α-methyl-3-iodo-5-androsten-17-acetate (8). Reduction of 8 with zinc metal and acid, followed by hydrolysis and oxidation with an oxidizing agent, such as chromium trioxides, yields the final product 7.

-continued
SCHEME 2A

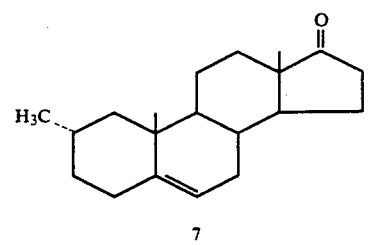

CARBON 4-ALKYLATION

A procedure for carbon-4 alkylation and the synthesis of 4α-methyl DHEA is given in Scheme 4.

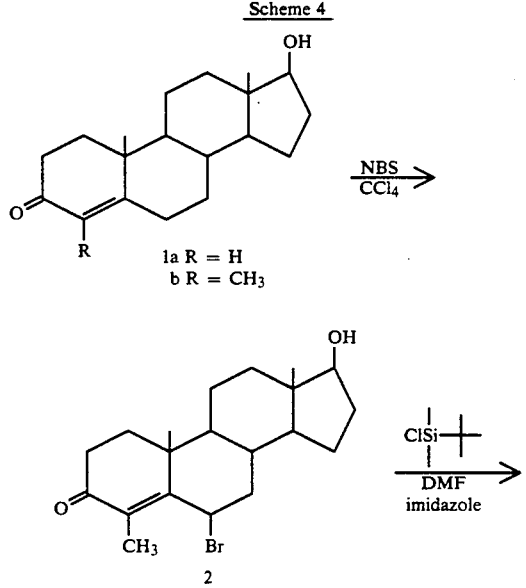

SCHEME 2A

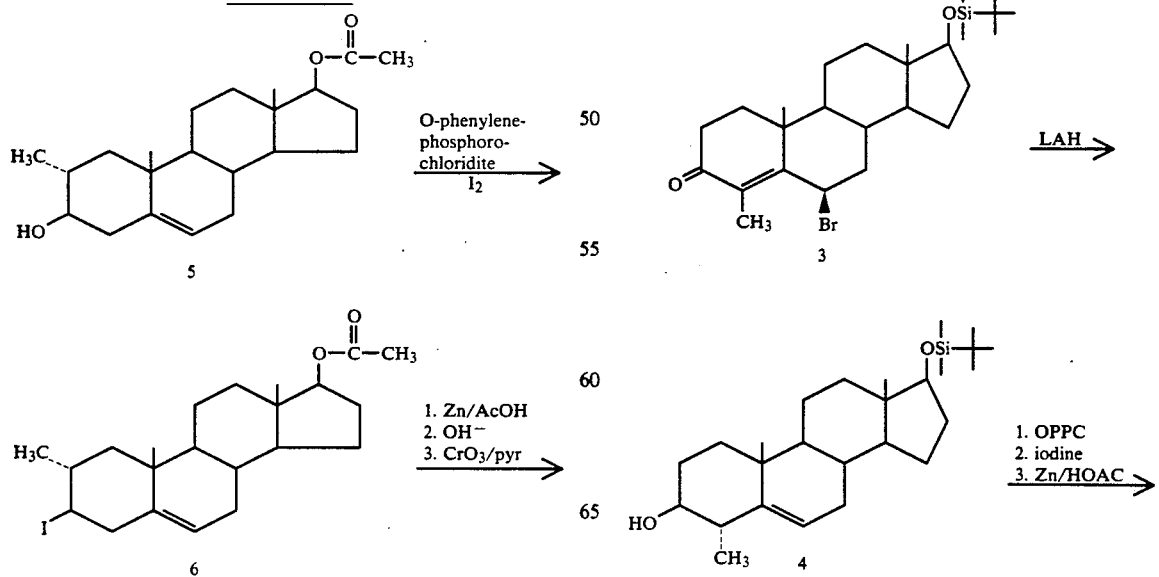

-continued
Scheme 4

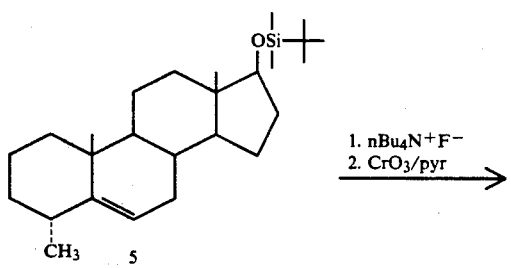

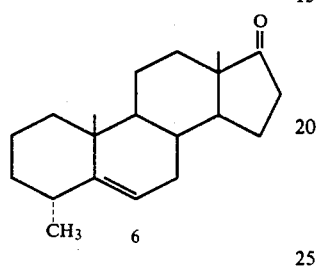

With reference to Scheme 4, alkylation of testosterone 1a using, for example, potassium t-butoxide and methyl iodide yields 4-methyltestosterone 1b. Allylic bromination of 4-methyltestosterone using N-bromosuccinimide in carbon tetrachloride yields the 6β-bromo-4-methylandrost-4-en-17-ol-3-one (2). Protection of the C-17 alcohol using a standard protecting group known in the art such as its t-butyldimethyl silyl derivative yields 3. Reduction of the ketone in 3 using, e.g., lithium aluminum hydride, concomitant with double bond migration and loss of bromide, yields 4. Reacting 4 with OPPC followed by iodine and Zn/AcOH yields the desoxy product 5. Removal of the protecting group and oxidation of the resulting C-17 alcohol yields the C-17 ketone 7.

ALKYLATION AT CARBON-6

Steroids may be alkylated at carbon-6 using the method of U. Stache and W. Fritsch, Liebigs Analen 1966, 697, 204. A procedure for carbon-6 alkylation is as follows:

-continued

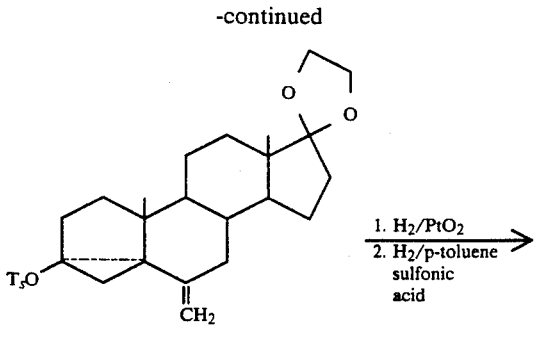

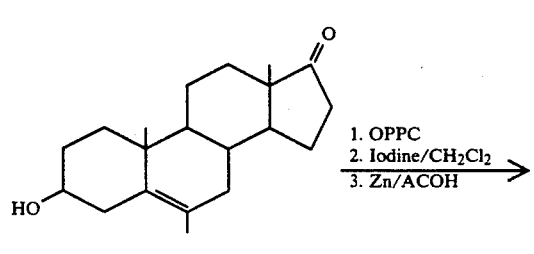

3α,5-Cyclosteroids such as 3α,5-cyclo-5α-androstan-6,17-dione 17 ketal 1 are readily available by solvolysis of steroidal 5-ene-3β-tosylates and mesylates followed by oxidation of the C-6 hydroxyl group. Alkenylation of 1 via a Wittig reaction, e.g., affords 6-methylene-3α,5-cyclo-5-α-androstan-17-one 17-ketal 2. Treatment of 2 with aqueous acid results in the addition of water and the formation of 3β-hydroxy-6-methylandrost-5-en-17-one, 3. Treatment of 3 with O-PPC/iodine followed by zinc in dilute acid, e.g., AcOH, affords the final product 4.

ALKYLATION AT C-7

A procedure for carbon-7 alkylation is as follows:

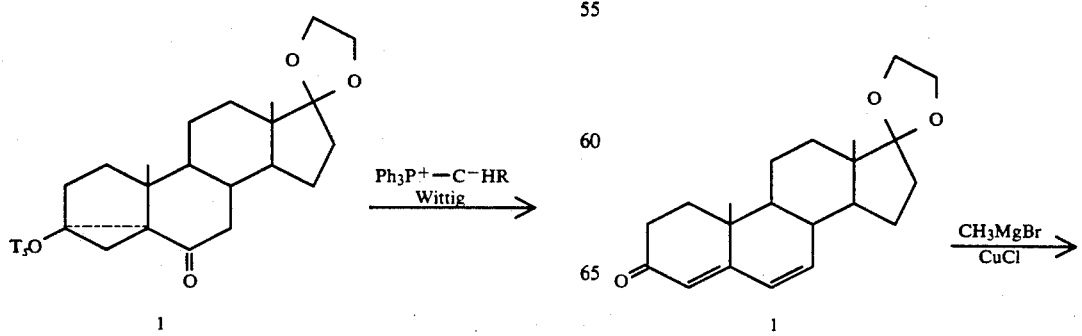

-continued

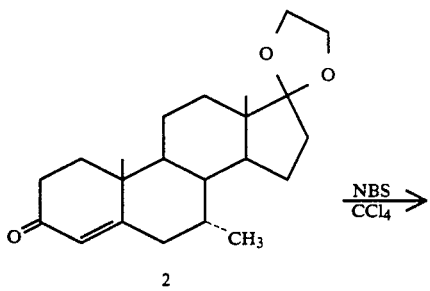
2

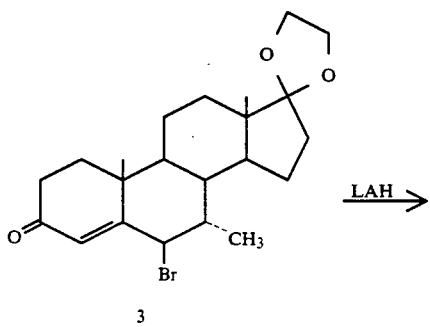
3

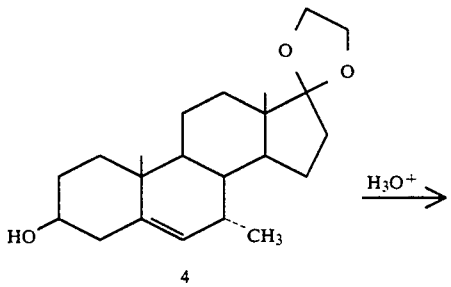
4

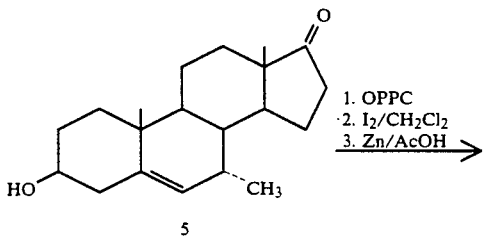
5

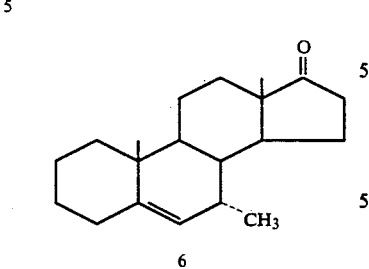
6

Alkylation of androsta-4,6-dien-3,17-dione 17 ketal 1 with methyl magnesium bromide in the presence of a Lewis acid, such as cuprous chloride, proceeds via conjugate addition to yield 7-α-methylandrost-5-en-3,17-dione 17 ketal 2. Allylic bromination of 2 using N-bromosuccinimide in carbon tetrachloride yields the 6-β-bromo-7α-methylandrost-4-en-3,17-dione 17 ketal 3. Lithium aluminum hydride reduction of the ketone in 3 with concomitant double bond migration and loss of bromide should yield 4. Deprotection of the C-17 ketone with aqueous acid yields 3β-hydroxy-7-α-methylandrost-5-en-17-one, 5. Higher homologues may be synthesized using the substituted Grignard reagent i.e. R=CH₃, C₂H₅, C₃H₇. The 7-β-epimer can be synthesized by treatment of 2 with DDQ-(dichlorodicyanoquinone) to generate another olefin at C-7. Catalytic reduction of this olefin should occur from the α face of the steroid to yield the 7β-methyl steroid i.e., 7-β-methylandrost-5-en-3,17-dione 17 ketal. Following the same sequence as above yields 3β-hydroxy-7β-methylandrost-5-en-17-one (5a). The desoxy derivative is prepared from 5 or 5a by substitution reactions known in the art, such as by reacting 5 or 5a with 0-phenylenephosphorochloridite and iodine, according to the procedure by Corey and Anderson, in JOC, 32, 4160 (1967). The product is then reacted with zinc in acid, e.g., acetic acid, to afford the 7-methyl-5-en-17-one derivative.

ALKYLATION AT CARBON-11

A procedure for alkylation at carbon-11 is as follows:

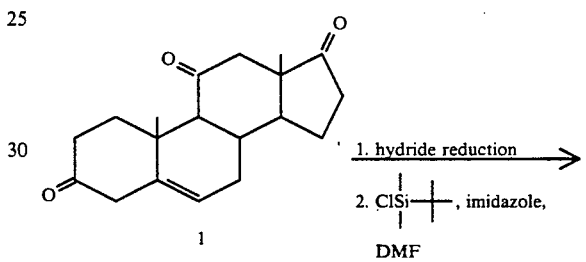
1

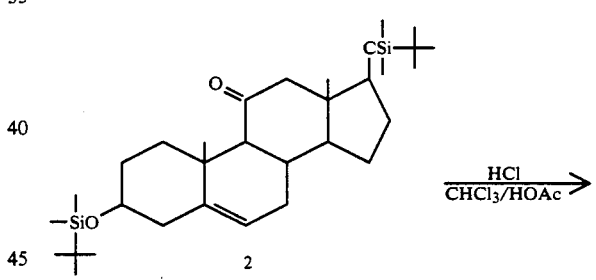
2

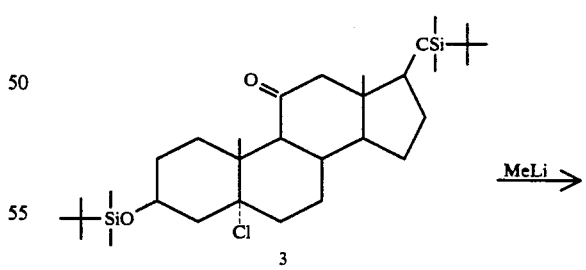
3

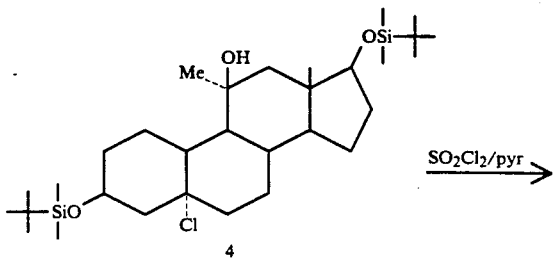
4

-continued

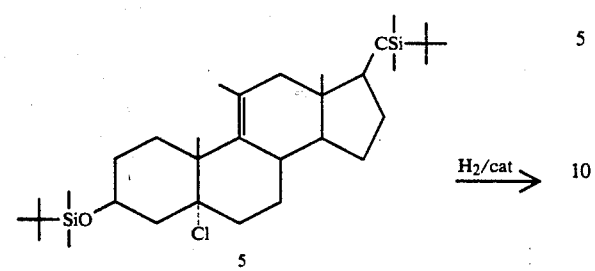

5

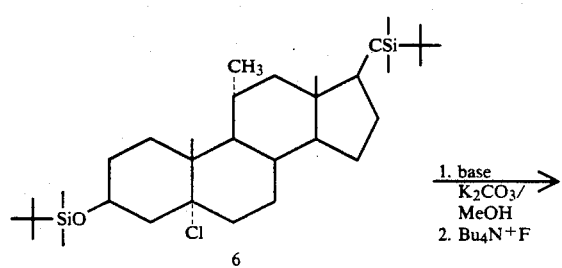

6

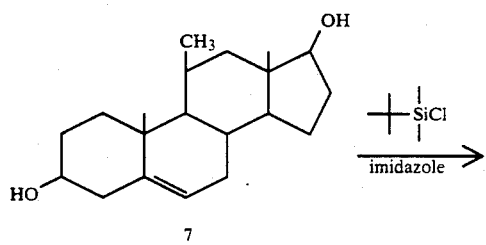

7

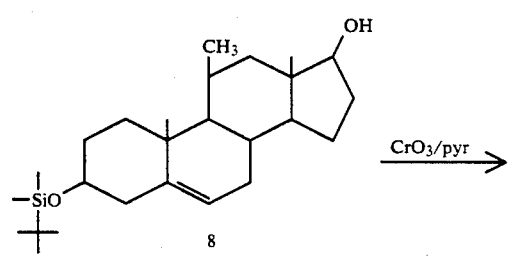

8

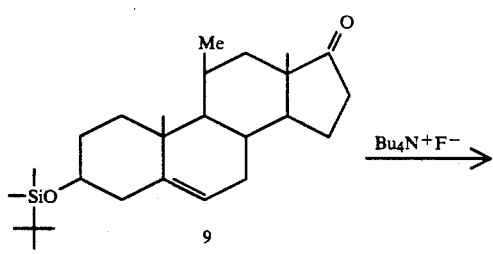

9

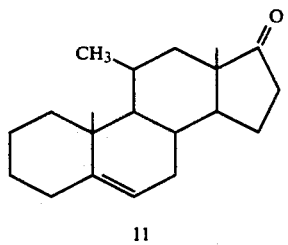

11

Due to the hindered nature of the C-11 ketone, selective reduction of androst-5-en-3,11,17-trione 1 with hydride should yield the C-3, C-17 dihydroxy steroid 2a, R=H which is protected, e.g., by its bis-(dimethyl-tert-butylsilyl) ether 2b R=Si(CH$_3$)$_2$t—Bu. Addition of hydrogen halide across the C-5 olefin, such as HCl, affords 5α-chloro-3β, 17β-dihydroxyandrost-5-en-11-one, 3,17-bis-(dimethyl-7-butylsilyl)ether 3. Alkylation with alkyl lithium, such as methyl lithium, proceeds from the less hindered face to yield 5α-chloro-11β-methyl-androstane-3β-11β,17β-triol-3,17-bis(dimethyl-t-butyl-silyl)ether 4. Reaction of 4 with thionyl chloride-pyridine yields the dehydration product 5. Catalytic hydrogenation of 5 yields the 11β-methyl product 6. Treatment of the chloro silyl ether 6 with base followed by tetrabutylammonium fluoride affords 11β-methyl-5-androsten-3β,17β-diol 7. Selective silylation yields 11β-methyl-5-androsten-3,17-diol-3-dimethyl-t-butylsilyl ether 8. Oxidation of the C-17 alcohol in 8 yields 9 and deprotection of the 3-alcohol yields 11-methylandrost-5-en-3β-ol-17-one 10. (11β-methyl DHEA). Using substitution and conversion reactions, such as reacting the hydroxy group with OPPC, iodine and zinc in dilute acid affords the final product 11. (11β-methyl-5-androsten-17-one).

ALKYLATION AT CARBON-16

A procedure for 16 alkylation is as follows:

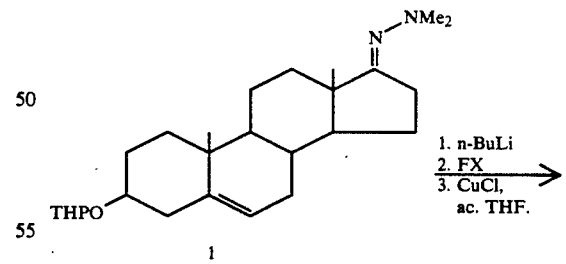

1

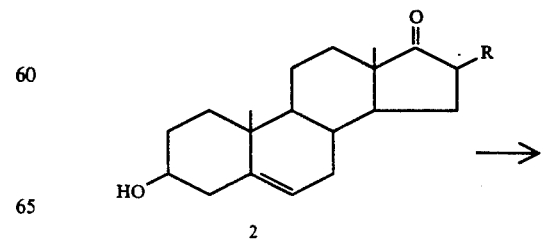

2

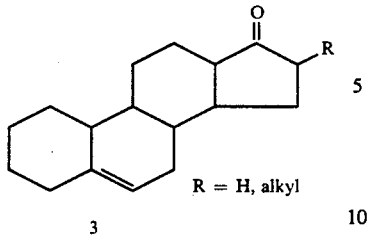

Alkylation of the 17-ketodimethylhydrazone of DHEA 3-tetrahydropyranyl ether using n-butyl lithium as the base followed by an alkyl halide RX, affords the 16α-alkylated steroid. Hydrazone cleavage with cuprous chloride in aqueous tetrahydrofuran led to regeneration of the C-17 ketone and concomitant cleavage of the tetrahydropyranyl ether results in the 16α-alkyl-3-hydroxy-androst-5-en-17-one (2). 2 is converted to 3 by procedures known to one skilled in the art, as e.g., reacting 2 with OPPC, then iodine, followed by zinc in acid.

HYDROXYLATION AT CARBON-16

A procedure for hydroxylation at carbon 16 is as follows:

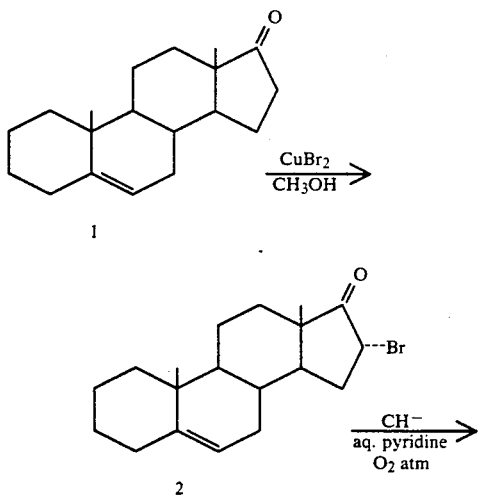

Halogenation of the 3-desoxy DHEA with an α-halogenating agent, such as bromine, chlorine, iodine, cupric bromide in methanol and the like, yields the 16α-bromo DHEA 2, which is in turn hydrolyzed with aqueous base in oxygen to afford the final product.

HALOGENATION AT CARBON-16

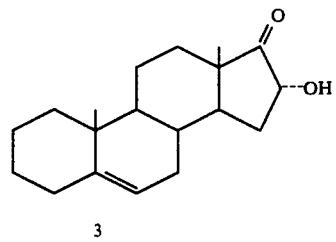

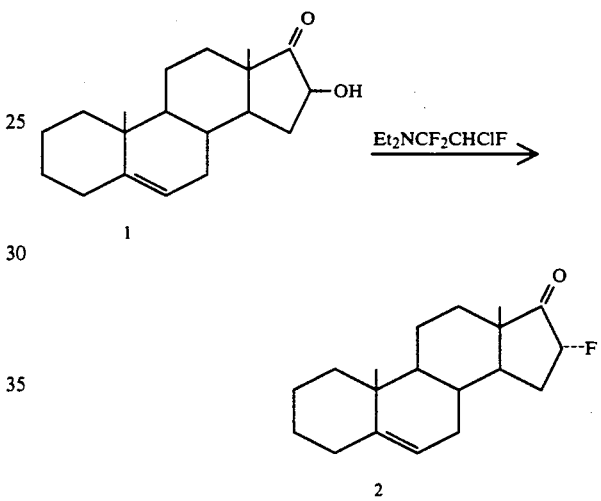

A procedure for halogenation at carbon-16 is as follows:

Reaction of 16β-hydroxy-5-androsten-17-one (1) with a fluorinating agent, such as diethyl (2-chloro-1,1,2-trifluoroethyl)amine affords 16α-fluoro-5-androsten-17-one 2.

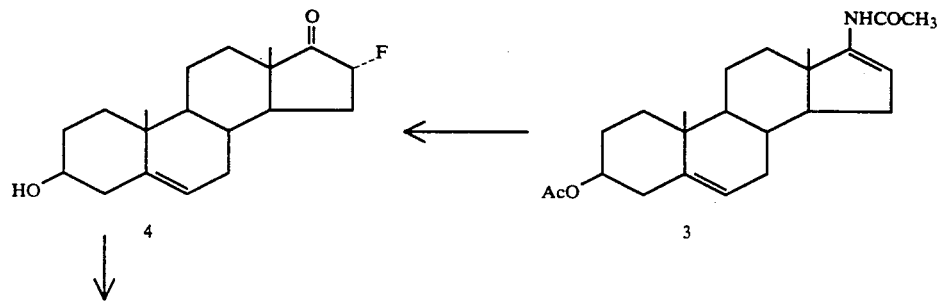

-continued

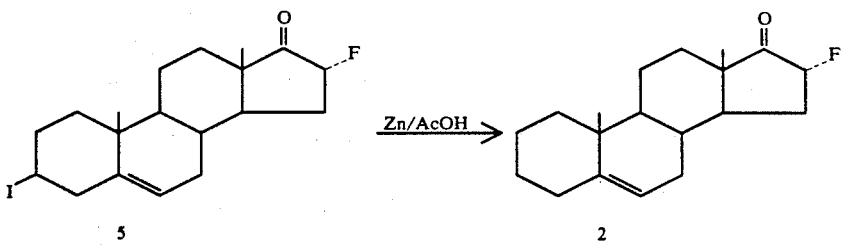

Alternatively, 2 could be prepared by treating an enamide, e.g., the enamide of Formula 3 with a fluorinating agent, such as perchloryl fluoride. Hydrolysis of the fluoro enamide acetate with aqueous acid gives 4. The 3-hydroxy group of 4 can be substituted with halogen by reactions known in the art, e.g., by reacting 4 with OPPC/$I_2$ to give 5. Reduction of 5 with acid in the presence of a metal, such as zinc in acetic acid, affords 2.

Finally, 2a can be synthesized from the corresponding halide prepared hereinbelow under the Finkelstein reaction conditions using fluorinating agents known in the art, such as AgF, $HgF_2$, KF in N-methyl pyrrolidone or tetramethylene sulfone and the like.

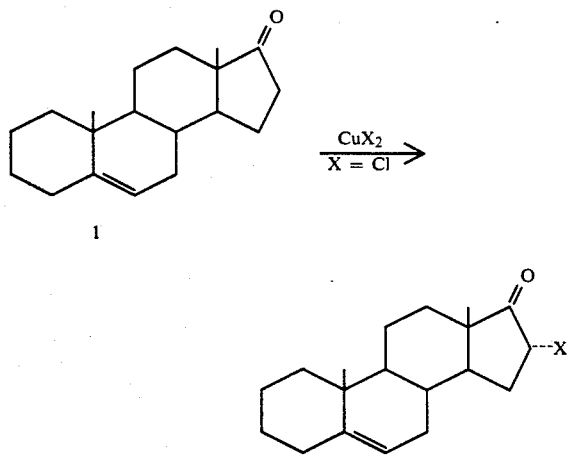

Reaction of androst-5-en-17-one 1 with cupric bromide yields 16α-bromo-androst-5-en-17-one, 2c[1]. Similarly reaction of 1 with cupric chloride yields 16-chloro-androst-5-en-17-one, 2b.
[1]E. R. Glazier J. Org. Chem. 1962, 27, 4397

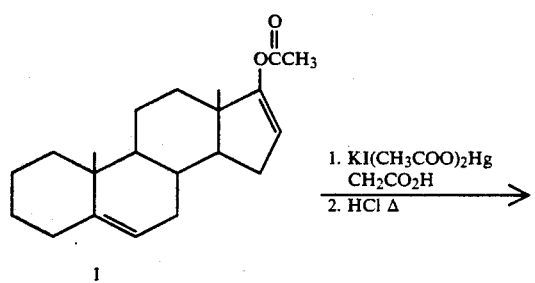

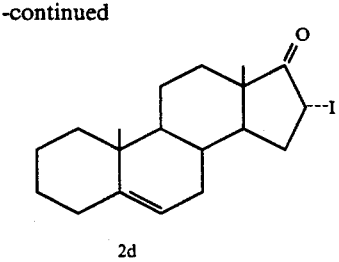

Reaction of 17-hydroxyandrosta-5,16-diene 17-acetate 1 with mercuric acetate followed by treatment with potassium iodide yielded the C-16α-iodide which hydrolyses with acid to yield 16α-iodoandrost-5-en-17-one, 2d. Reaction of 2d with silver fluoride yields the 16α-fluoroandrost-5-en-17-one, 2a.

In addition, the reaction of 2c with NaI/acetone overnight results in a mixture of 16α- and 16-β-I-androst-5-en-17-ones.

Similarly, using the appropriate starting materials, the following product can also be prepared:
16βmethyl-16α-fluoroandrost-5-en-17-one.

The androstan-17-one derivatives of the present invention can also be prepared using synthetic pathways known in the art. For example, catalytic hydrogenation of the corresponding 5-androsten-17-one derivatives affords the various 5-androstan-17-one derivatives. Alternatively, the 16-halo and 16-hydroxy-5-androstan-17-one can be prepared by substituting 5-androstan-17-one for 5-androstan-17-one and following the procedures in the sections entitled "Hydroxylation at carbon-16" and "Halogenation at carbon-16," discussed supra. The 5-androstan-17-one can in turn be prepared from catalytic hydrogenation of 3-desoxy DHEA.

The following examples further illustrate the invention:

EXAMPLE I

A. 16α-Fluoro-5-Androsten-17-one

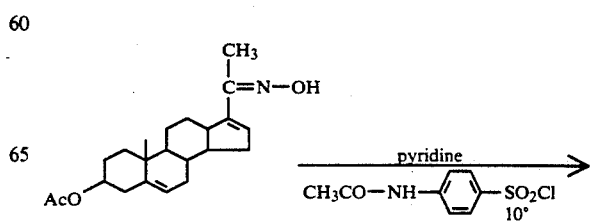

-continued

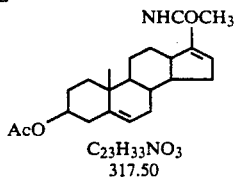

C23H33NO3
317.50

To a solution of the oxime (30.0 g) in 120 ml of pyridine at 10° while stirring magnetically was added 30.0 g of p-acetamidobenzenesulfonyl chloride. The solution was stirred for 2 hours while maintaining the temperature at 10°±2° C. The clear yellow-orange reaction mixture was added to 1 L of ice water and the resulting orange, oily suspension was extracted with 500 ml of methylene chloride. The organic layer was washed with water, filtered through anhydrous sodium sulfate, and concentrated to dryness. Several additions of toluene followed by drying in vacuo served to remove most of the pyridine. The orange, semi-crystalline residue was digested with 500 ml of methylene chloride. The insoluble fraction was filtered off, washed with methylene chloride, and discarded. To the filtrate was added an equal volume of ethanol. Concentration in an air stream to approximately 300 ml afforded 21.1 g of yellow needles. mp 228°–230°. Fractional crystallization of the mother liquors gave an additional 1.90 g, mp 227°–230°. Yield=23.0 g (76.7%); λmax 3320, 1530 (NHCOCH3), 1732, 1240, 1030 cm⁻¹ (3β-acetate).

B. Reaction of 17-acetamide-5,16-androstadien-3B-ol Acetate with Perchloryl Fluoride in Pyridine (See S. Nakanishi, J. Med. Chem 7, 108 (1964))

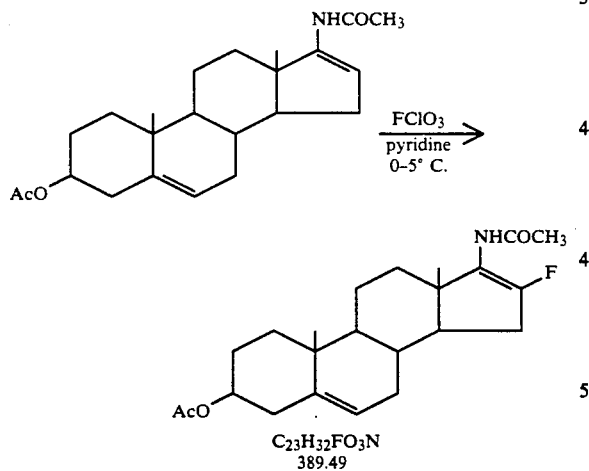

C23H32FO3N
389.49

Into a solution of the enamide (7.50 g) in pyridine (400 ml) at 0°–5° C. was bubbled perchloryl fluoride for 4 minutes. The reaction mixture was added to 1500 ml of ice water and concentrated hydrochloric acid was added slowly with magnetic stirring to pH 1-2. The colorless, crystalline precipitate was filtered off and washed thoroughly with water. Recrystallization from methylene chloride-isooctane gave 4.40 g of light yellow prisms, mp 165°–169°, λ max 3250, 1635 (NHCOCH3) 1735, 1240, 1030 cm⁻¹ (3B acetate). Fractional crystallization of the mother liquors gave an additional 0.52 g, mp 162–165. Yield=4.92 g (66%) The final mother liquor residue (3.03 g) was sufficiently pure for acid hydrolysis to the 16α-fluoro 17-one (see C).

C. Acid Hydrolysis of fluroenamide Acetate to 16α-Fluoro-3β-Hydroxy-5-androsten-17-one

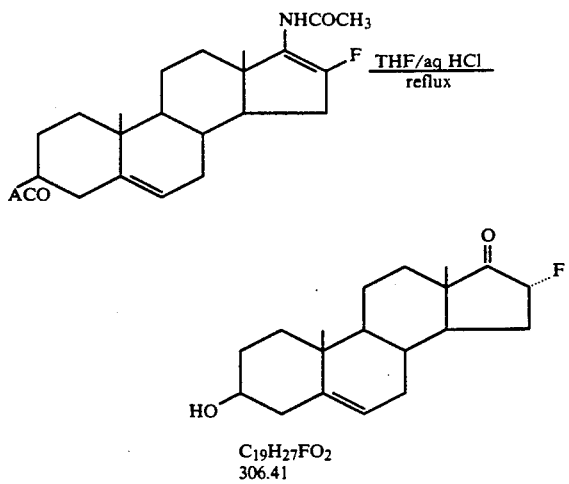

C19H27FO2
306.41

To a solution of the fluoroenamide acetate (4.20 g) in 150 ml each of anhydrous tetrahydrofuran and water was added 15 ml of concentrated hydrochloric acid. The mixture was refluxed for 14 hours, then partitioned between methylene chloride and water. The organic layer was washed with water, filtered through anhydrous sodium sulfate, and concentrated to dryness. Crystallization from acetone-isooctane furnished 3.16 g of fine needles, mp 145°–147° (96% yield), λ max 3350 (hydroxyl), 1752 cm⁻¹ (16-fluoro-17-one).

D. Preparation of 3β-Iodo-16α-Fluoro-5-Androsten-17-one (See Corey and Anderson, JOC 32, 4160, 1967)

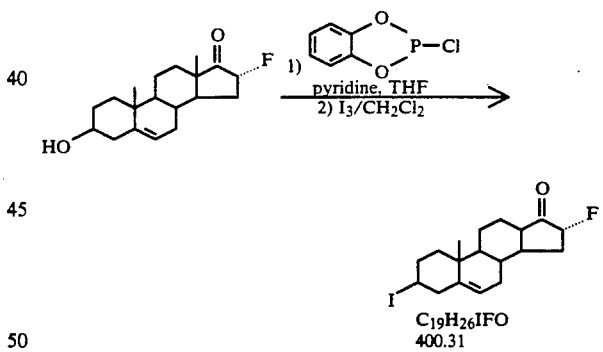

C19H26IFO
400.31

To a solution of pyridine (0.41 ml) and 0-phenylenephosphorochloridite (0.6 ml) in anhydrous THF (10 ml) at 0° was added 1.53 g (5 mmoles) of the hydroxyfluoroketone in 10 ml of THF. After stirring for two hours at room temperature, the pyridinium chloride was filtered off and washed with THF. After removal of the solvent in vacuo, the crude phosphite ester was dissolved in 25 ml of methylene chloride and treated with 1.27 g of iodine for three hours at room temperature. The reaction mixture was washed successively with 15 ml of 1N sodium hydroxide and water, filtered through anhydrous sodium sulfate, and the product was crystallized from methylene chloride/methanol in a yield of 1.85 g (92.5%), mp 165°–167° (dec.) λ max 1755 cm⁻¹ (16-fluoro-17-one).

E. Reaction of Iodofluoroketone with Zinc/Acetic Acid

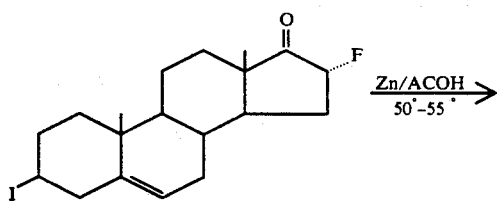

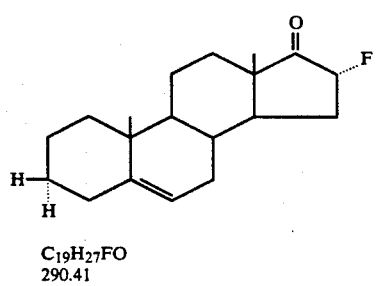

C₁₉H₂₇FO
290.41

To a solution of 3β-iodo-16αfluoro-5-androsten-17-one (1310 mg, 3.28 mmoles) in 40 ml of glacial acetic acid was added 2.62 g of zinc dust. The mixture was stirred magnetically at 50°–55° for one hour, then partitioned between methylene chloride and water. The organic layer was washed with dilute sodium hydroxide and water, filtered through anhydrous sodium sulfate and concentrated to dryness. Crystallization from methylene chloride-methanol gave 630 mg of a colorless platelet mp 167°–169°. Fractional crystallization of the mother liquors gave an additional 140 mg, mp 165°–167°, raising the yield to 770 mg (81.0%); λ max 1752 cm$^{-1}$ (16-fluoro-17-one).

EXAMPLE II

Preparation 16αBromo-5-androsten-17-one

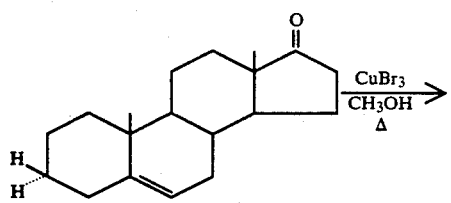

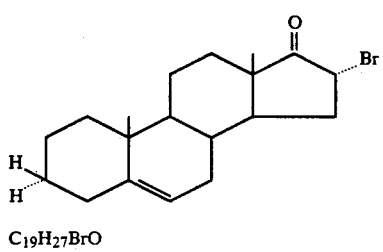

C₁₉H₂₇BrO
315.11

A solution of 5-androsten-17-one (10.88 g, 40 mmoles) in methanol (2 L) was refluxed with 26.8 g (120 mmoles) of CuBr₂ for 17 hours. The reaction mixture was added to 2 L of water and the resulting crystalline suspension was stirred several hours at 5° C. The product was filtered off, washed with water and recrystallized from methanol as colorless needles: 7.95 g, mp 172°–174°, 2.00 g, m.p. 165°–168°. High performance liquid chromatography (HPLC) of the mother liquor using ethyl acetate-n-hexane as eluent, afforded an additional 0.58 g of 16α-Bromide, raising the yield to 10.53 g (75.0%). In addition, 800 mg (5.7%) of 16B-Bromo-5-androsten-17-one, mp 149.5° to 152°, was obtained. Also obtained was 75 mg of 16, 16-dibromo-5-androsten-17-one, mp 194°–195°.

EXAMPLE III

Synthesis 16αHydroxy-5-androsten-17-one

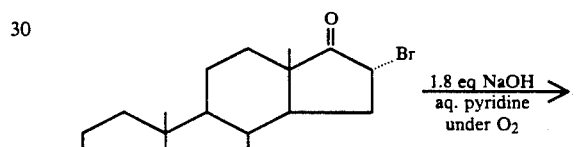

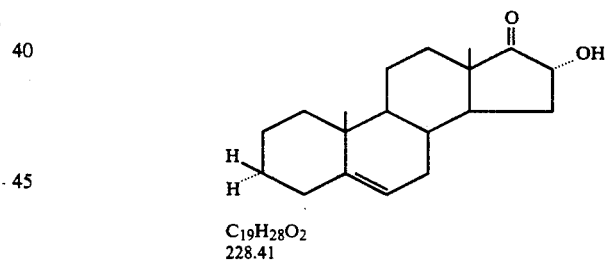

C₁₉H₂₈O₂
228.41

To a solution of 16α-Bromo-5-androsten-17-one (7.92 g, 20 mmoles) in pyridine (300 ml) and water (64 ml) in an oxygen atmosphere was added 36 ml (36 mmoles) of 1N NaOH. After stirring the mixture for 15 minutes at room temperature under O₂, it was added to 1 L of ice water containing 330 ml of concentrated HCl. The crystallized precipitate which formed was filtered off, washed with water, and recrystallized from methanol as leaflets (2, 80 g), mp 168°–172°. HPLC of the mother liquor on a silica gel column using isopropyl alcohol n-hexane as eluent furnished an additional 1.4 g of light yellow prisms, mp 170°–174°. The total yield of 16α-ol was 3.94 g (68.4%).

EXAMPLE IV

Preparation of 16α-methyl-5-androsten-17-one, 16β-methyl-5-androsten-17-one, and 16β-methyl-16α-fluoro-5-androsten-17-one

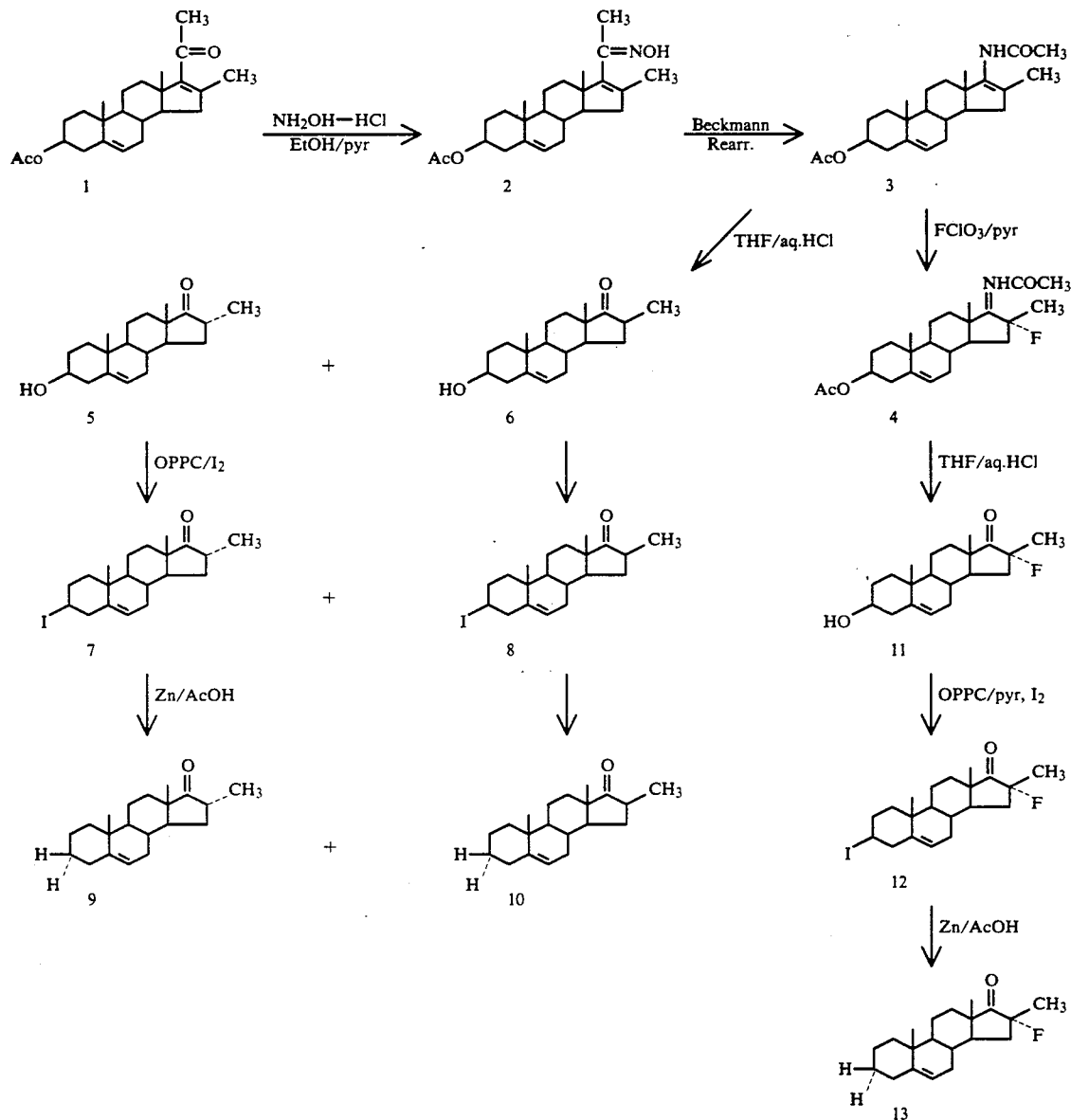

I. Preparation of 16-methyl-3-acetoxy-5,16-pregnadien-20-one-oxime (2)

A solution of 16-methyl-3β-acetoxy-5,16-pregnadien-20-one (3.70 g, 10 mmoles) was refluxed in a mixture of ethanol (100 ml) and pyridine (10 ml) containing 3.50 g (50 mmoles) of hydroxylamine hydrochloride for one hour. The reaction mixture was added to water and the crude product was filtered and washed with water. Solution in methylene chloride, filtration through anhydrous sodium sulfate, and concentration to dryness in vacuo gave the crude oxime.

II. Beckmann Rearrangement of I

Treatment of the crude oxime from 3.70 g of 20-one in 15 ml of pyridine with 3.75 g of p-acetamidobenzenesulfonyl chloride was carried out for 2 hours at 10°. The reaction mixture was added to ice water, furnishing a filterable solid which was washed thoroughly with water. The dried product was 17-acetamido-16-methyl-5,16-androstadien-3β-ol acetate (3), weighing 3.88 g.

III. Reaction of 3 with Perchloryl Fluoride/Pyridine

A solution of the 16-methyl enamide acetate (1.94 g) in pyridine (100 ml) was treated with FClO$_3$ for 4 minutes as described in Example IB. The reaction mixture was added to ice water and cold, concentrated HCl was added until the reaction mixture has a pH 1. The resulting precipitate was filtered off and washed with water. The product was dissolved in methylene chloride and filtered through anhydrous sodium sulfate, affording the crude fluoro methyl enamide acetate (4).

IV. Preparation of 16β-methyl-16α-fluoro-3-hydroxy-5-androsten-17-one (11)

A solution of (4) in tetrahydrofuran (100 ml) and water (100 ml) was refluxed in 10 ml of concentrated hydrochloride acid for 14 hours. The reaction mixture was partitioned between methylene chloride and water and the organic layer was filtered through anhydrous sodium sulfate. The crude hydroxy methyl fluoro ketone was subjected to preparative HPLC on a silica gel column in isopropyl alcohol/n-hexane. Crystallization of the major product from methanol gave long needles (420 mg, mp 177-180; 90 mg, mp 170-173). The mother liquor residue (350 mg) from the crystalline product was employed in the next step.

V. Preparation of 16-methyl-16-fluoro-5-androsten-17-one

The crude 3-ol (4, 350 mg) from the previous step was added in 5 ml of methylene chloride to 5 ml of methylene chloride containing 90 μl of pyridine and 130 μl of 0-phenylenephosphorochloridite at 0° C. After standing for 2 hours at room temperature the crude phosphite was treated with 280 mg of iodine and the resulting mixture was stirred magnetically at room temperature for 2½ hours. The reaction mixture was washed successively with 1N NaOH (6 ml) and water (10 ml) filtered through sodium sulfate and dried. The crude 3-iodide (12) mixture (140 mg) was treated in 2 ml of acetic acid with 300 mg of zinc dust for 1 hour at 65°-70° C. After partitioning the reaction mixture between methylene chloride and water, the crude product was subjected to preparative HPLC on a silica gel column in ethyl acetate hexane.

A minor, more mobile product crystallized from aqueous acetone as platelets (12.5 mg), mp 122°-123°. Its infrared spectrum was consistent with a 16α-methyl-16β-fluoro-5-androsten-17-one structure. The major, less mobile product crystallized from methanol as needles (48.5 mg), mp 173°-175°. Its infrared spectrum was consistent with 16β-methyl-16α-fluoro-5-androsten-17-one (13).

VI. Preparation of 16-α and 16β-methyl-5-androsten-17-ones

The crude methyl enamide acetate (1.94 g) was refluxed in 100 ml each of THF and water with 10 ml of concentrated HCl for 3½ hours. Following the usual work-up the crude hydroxy methyl ketones (5 and 6) were analyzed as the 3-acetates. In isooctane-ethyl acetate (21:4) there was a roughly 3:1 mixture of polar ($R_f$ 0.17) and mobile ($R_f$ 0.21) products, representing a mixture of the 16α-methyl and 16β-methyl-17-ones, respectively. Crystallization of the original 3-hydroxy mixture gave 425 mg of pure 16β-methyl-5-androsten-17-one (6), mp 168°-170°. The mother liquor residue (660 mg) represented a mixture of 16-α and 16β-methyl-3-hydroxy-17-ones (5 and 6). A solution of this mixture plus 6 ml of methylene chloride was added to 6 ml of methylene chloride containing 180 μl of pyridine and 260 μl of 0-phenylenephosphorochloridite at 0° C. and the mixture stood at room temperature for 2 hours. After addition of iodine (560 mg) to the crude phosphite, the reaction proceeded for 2½ hours at room temperature. The reaction mixture was washed with 10 ml of 1N NaOH and 10 ml of water. The mixture of iodides (7 and 8) was subjected to preparative HPLC on a silica gel column in ethyl acetate hexane. The more mobile product, designated 16α-methyl-3β-iodo-5-androsten-17-one (7) crystallized from methanol as needles (120 mg), mp 150°-151.5°.

λmax 1728 cm$^{-1}$ (16α-methyl-17-one) (See Noef, et al. JOC 43, 4579, 1978).

The less mobile product, designated 16β-methyl-3β-iodo-5-androsten-17-one (8) crystallized as needles (200 mg) from methanol, mp 151-153, λmax 1734 cm$^{-1}$ (16β-methyl-17-one according to Noef).

Treatment of 16α-methyl-3β-iodo-5-androsten-17-one (7) (90 mg) in 2.5 ml of acetic acid with 180 mg of zinc dust was carried out for one hour at 65°-70°. Crystallization of the product from aqueous acetone gave 40 mg of needles, mp 92°-95° C. Infrared analysis was consistent with 16α-methyl-5-androsten-17-one (9).

Treatment of 16β-methyl-3β-iodo-5-androsten-17-one (8, 200 mg) in 5 ml of acetic acid with 400 mg of zinc as in the preparation of 9 gave 95 mg of platelets from methanol, mp 102-103. IR analysis confirmed the 16β-methyl-5-androsten-17-one (10) structure.

EXAMPLE V

Preparation of 16αBromo-5-androstan-17-one

A. Method 1: Preparation of 3α-Iodo-5α-Androstan-17-one

Epiandrosterone (1.45 gms, 5 mmole) and 10 ml of THF was added to 0.41 ml of pyridine, 0.60 ml of 0-Phenylenephosphorochloridite and 10 ml of THF at 0° C. The mixture was stirred for two hours at room temperature. After filtering off the precipitated pyridinium chloride, the solvent was removed in vacuo, affording the crude phosphite ester. The residue was treated in 25 ml of methylene chloride with 1.27 grams (5.0 mmole) of iodine, and the mixture was stirred at room temperature for two and one half hours. Successive washings with 15 ml of 1N NaOH and water followed by filtration of the organic layer through anhydrous sodium thiosulfate afforded the crude 3α-iodide derivative. Crystallization from methanol combined with the HPLC of the mother liquor afforded a total of 0.82 grams of the above-identified product, melting point 124°-127°. Significant dehydrohalogenation by-products of the reaction were the 2-androstene-17-one and 3-androstene-17-one.

Method 2: Preparation of 3β-Iodo-5α-Androstan-17-one

To a solution of 1.6 g of epiandrosterone in 12 ml of pyridine was added 1.6 g of TsCl. The mixture stood for 13 hours at room temperature. After the addition of water, the product was extracted with methylene chloride. The organic layer was washed with cold dilute HCl, then water, affording a crude semi-crystalline tosylate. This material was refluxed in 100 ml acetone containing 10 grams of sodium iodide for 22 hours. The reaction mixture was partitioned between methylene chloride and water and the crude product was crystallized from methanol, yielding 920 mg of 3βIodo-5-α-androstan-17-one opaque prisms, mp 147°-150° C. The TLC of the crystalline material and its mother liquor in isooctane ethyl acetate (22:3) showed the crystalline material to be homogenous. ($R_f$=0.16). The material absorbed in the UV at 254 nm. (UV positive).

The mother liquor consisted of a ternary mixture, with the crystalline product being the most polar (lowest $R_f$). A second UV positive component with a similar $R_f$ ($R_f$=0.20) as the 3α-Iodide and a third (UV negative) more mobile component with a larger $R_f$ ($R_f$=0.25) as the olefinic mixture obtained in Method I were also isolated.

B. Preparation of 5α-androstan-17-one

Method 1

0.84 grams of the 3α-iodoantrostane-17-one in 25 ml of acetic acid was heated with 1.68 grams of zinc dust at 70°-75° for one hour with magnetic stirring. The reaction mixture was cooled, diluted with water and the crystalline precipitate resulting therefrom was filtered off and washed with water. The residue was leached with methylene chloride and the product was crystallized from aqueous methanol as platelets (480 mg) in a yield of 83.5%. Melting point 121°–121.5°. Similar reaction of 3β-iodo-5α-androstan-17-one with zinc in acetic acid, afforded 5α-androstan-17-one in comparable yields.

Method 2

To a solution of 2.5 g of 5-androstene-17-one in 500 ml of ethanol was added 500 mg of 5% Pd on C and the mixture was exposed to a hydrogen atmosphere while stirring for 2.5 hours. The catalyst was filtered off and the residue from the filtrate had the same IR spectra as the material produced in B, Method 1.

C. 16α-Bromo-5-α-androstan-17-one 2.5 grams of the product from part B in 450 ml of methanol was refluxed with 6.06 grams (27.18 mmole) of CuBr$_2$ for 17½ hours. After the addition of an equal volume of water, the crystalline precipitate was filtered off and washed with water. Crystallization from methylene chloride/methanol gave 2.03 grams of the bromide as colorless prismatic needles, melting point 194°–196° (63% yield).

Alternatively, the above product may be prepared by catalytic hydrogenation over 5% palladium on carbon of 16α-Bromo-5-androsten-17-one, in accordance with the procedure in V B, Method 2 hereinabove.

EXAMPLE VI

Preparation of 16α-hydroxy-5α-androstan-17-one

A solution of 16α-Bromo-5-androstan-17-one (706 mg, 2 mmole,), as prepared in accordance with the procedure in Example V, 60 ml of pyridine and 16 ml of water was treated with 3.6 ml (3.6 mmole) of 1N sodium hydroxide under oxygen. After stirring magnetically at room temperature for 15 minutes in an oxygen atmosphere, the clear yellow reaction mixture resulting therefrom was added to ice water containing 66 ml of concentrated HCl. The product was extracted with methylene chloride and was crystallized as large prisms from methanol 375 mg, melting point 157°–158° C.

EXAMPLE VII

Preparation of 16α-fluoro-5α-androstan-17-one

Method 1

To a stirred solution of 500 mg of 16α-Bromo-5-androstan-17-one, prepared in accordance with the procedure of Example V, in 10 ml of DMSO was added 500 mg of 18-crown-6 ether and 1500 mg of KF. The solution was heated to 85°–90°. After 6 hours, the mixture was partitioned between methylene chloride and water and was subjected to HPLC in an ethyl acetate-hexane gradient system. Crystallization from methanol of the more mobile component gave 23 mg of starting material (melting point 188°–190° C.). Crystallization from methanol of the less mobile component gave 41 mg of plates, the IR of which is consistent with the final product.

Method 2

250 mg of 16β-fluoro-5-α-androsten-17-one in 50 ml of ethanol was treated with 50 mg of 5% palladium on carbon and hydrogen gas for 2½ hours. The reaction mixture, as indicated by the IR, is compatible with 16β-fluoro-5α-androstan-17-one. This crude product was treated with 5 ml methanol and 5 ml of 1N methanolic KOH for one hour. The mixture was partitioned between methylene chloride and water and subjected to HPLC as indicated above. Crystallization of the less mobile component from methanol gave 30 mg of 16α-fluoro-5α-androstan-17-one as prismatic needles, melting point 148°–150° C.

Method 3

To a solution of 16α-fluoro-5α-androstene-17-one (1100 mg) in ethanol (220 ml) was added 220 mg of 5% Pd on carbon. The mixture was stirred in a hydrogen atmosphere for 1 hour at room temperature. The catalyst was filtered off and washed with ethanol. The residue from the combined filtrate was recrystallized from methanol, giving 770 mg, m.p. 146°–148.5° C. The IR spectrum was identical with that of 16α-fluoro-5-αandrostan-17-one prepared hereinabove.

The following compounds have been tested in the following biological assays. These compounds will be designated in the following tables by the designation under the chemical formulae:

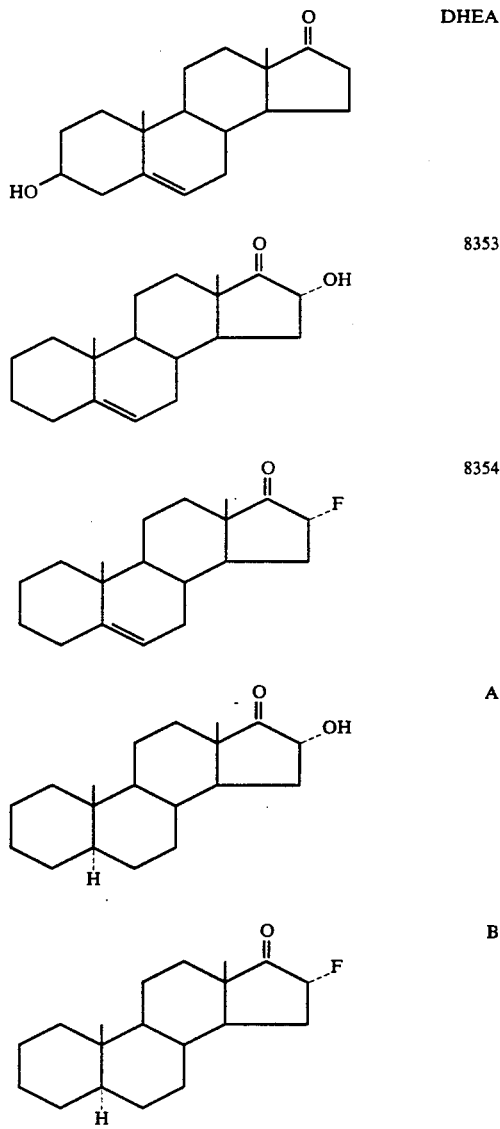

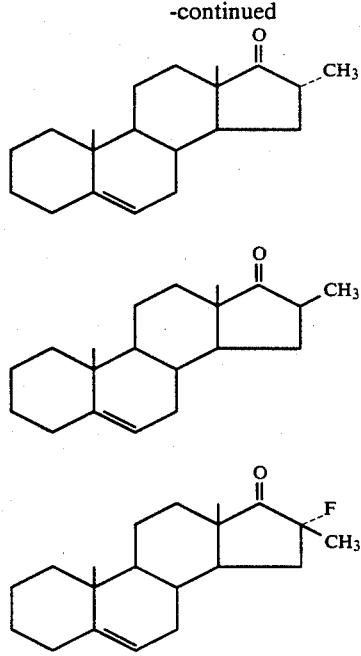

C

D

F

Inhibition of G6PDH

The compound listed below are screened as inhibitors of purified bovine adrenal G6PDH activity as one predictor of cancer preventive action. The assay for testing the inhibition of purified bovine adrenal G6PDH is according to the procedure by Oertell, G. W. and Rebelein, I. in Biochem. Biophys. Acta, 184, 459–460 (1969). The results are given below in Table I:

TABLE 1

G6PDH INHIBITION TEST

| Compounds Tested | | Percent Inhibition |
|---|---|---|
| DHEA | $10^{-5}$M | 53, 57 |
| | $10^{-6}$M | 17, 17 |
| 8353 | $10^{-5}$M | 77, 77 |
| | $10^{-6}$M | 30, 36, 29, 38 |
| 8354 | $10^{-5}$M | 79, 83 |
| | $10^{-6}$M | 75, 77 |
| A | $10^{-5}$M | 94, 94, 92, 91 |
| | $10^{-6}$M | 72, 72 |
| | $10^{-7}$M | 17, 25 |
| B | $10^{-5}$M | 96, 96, 96, 96 |
| | $10^{-6}$M | 82, 84 |
| | $10^{-7}$M | 36, 36 |
| C | $10^{-5}$M | 54, 52 |
| | $10^{-6}$M | 33, 31 |
| | $10^{-7}$M | 20, 24 |
| D | $10^{-5}$M | 44, 47 |
| | $10^{-6}$M | 13, 20 |
| F | $10^{-5}$M | 82, 82 |
| | $10^{-6}$M | 66, 69 |
| | $10^{-7}$M | 28, 34 |

Estrogenic and Anti-Estrogenic Activity

Female CD rats, 26–27 days old, were injected subcutaneously for 3 days with one of the compounds of the present invention at 60 mg/kg in propylene glycol. Controls received propylene glycol alone. On the 4th day, the rats were killed and the uteri were dissected out and weighed. The results are given in the Tables below:

TABLE 2

ESTROGENIC ACID ANTI-ESTROGENIC ACTIVITY
Compound 8353 was tested for estrogenic and anti-estrogenic action.

| Group | Mean Uterine Weight ± S.D. (mg/100 gm body weight) |
|---|---|
| Control | 2.02 ± 0.28 (n = 6) |
| DHEA (60 mg/kg) | 4.17 ± 0.48 (n = 6)* |
| 8353 (60 mg/kg) | 2.15 ± 0.17 (n = 6) |

*Significantly greater than control group, p < .001

TABLE 2a

ESTROGENIC AND ANTI-ESTROGENIC ACTIVITY
Compound 8354 was tested for estrogenic and anti-estrogenic action:

| Group | Mean Uterine Weight ± S.D. |
|---|---|
| Control | 1.95 ± 0.22 (n = 6) |
| DHEA (60 mg/kg) | 3.93 ± 0.71 (n = 5)* |
| 8354 (60 mg/kg) | 1.93 ± 0.29 (n = 5) |

*Significantly greater than control group, p < 0.001

BACKGROUND INFORMATION ON ACTIONS OF DMBA AND TPA

Skin tumors can be induced in the mouse either by weekly application of a carcinogen such as 7,12-dimethylbenzylanthracene (DMBA), or alternatively, by a single subthreshold dose of the carcinogen followed by twice weekly applications of the tumor promoter tetradecanoylphorbol-13-acetate (TPA). In order to exert its carcinogenic effect, DMBA must be metabolized by an NADPH-dependent mixed-function oxidase to chemically reactive intermediates which bind covalently to DNA and produce mutations leading to malignant transformation. Dehydroepiandrosterone (DHEA) and 3B-methylandrost-5-en-17-one inhibit 7,12-dimethylbenz(a)anthracene (DMBA)-initiated and 12-O-tetradecanoylphorbol-13-acetate (TPA)-promoted skin papilloma formation in mice, Carcinogenesis, 5, 464–466 and DHEA inhibits the rate of binding of topically applied $^3$H-DMBA to A/J mouse skin DNA (Table 4). The potent androgen, testosterone, is without inhibitory effect. This effect of DHEA very probably is a result of the inhibition of G6PDH and lowering of the intracellular pool of NADPH, which is a co-factor for the mixed-function oxidase activation of DMBA. Topical DHEA or 3β-methylandrost-5-en-17-one application also inhibits DMBA produced papillomas and carcinomas in the complete carcinogenesis model (Pashko, L. L. Hard, G. C.; Rovito, R. J.; Williams, J. R.; Sobel, E. L.; and Schwartz, A. G. (1985). Inhibition of 7,12-dimethylbenz(a)anthracene induced skin papillomas and carcinomas by dehydroepiandrosterone and 3B-methylandrost-5-en-17-one in mice, Cancer Res., 45, 164–166).

Tumor promoters, such as TPA, stimulate hyperplasia and DNA synthesis when applied to the skin, and it is believed that this stimulation is an important step in the enhancement of tumorigenesis. This stimulation of epidermal DNA synthesis rate by TPA can be demonstrated by an enhanced rate of $^3$H-thymidine incorporation in mouse epidermis 20 hours after TPA application. Again, topical DHEA treatment abolishes this stimulation (Table 5).

The inhibition of the TPA stimulation of epidermal $^3$H-thymidine incorporation by DHEA may also result from G6PDH inhibition. The pentose-phosphate pathway provides both ribose-phosphate for ribonucleotide synthesis as well as NADPH which is needed both for the reduction of folic acid to tetrahydrofolic acid (required for ribonucleotide and thymidylate synthesis) as well as for the activity of ribouucleotide reductase. DHEA, over a range of $10^{-5}M$ to $10^{-4}M$, slows the growth of many different cell lines in culture. One HeLa cell strain, TCRC-2, is particularly sensitive to DHEA-induced growth inhibition. This growth inhibition can be almost completely overcome by adding to the culture medium a mixture of the deoxynucleosides of adenine, guanine, cytosine, and thymine, which is consistent with the hypothesis that DHEA inhibits cell growth through G6PDH inhibition (Dworkin, C. R., Gorman, S. D., Pashko, L. L., Cristofallo, V. J. and Schwartz, A. G. (1986). Inhibition of growth of HeLa and WI-38 cells by dehydroepiandrosterone and its reversal by ribo-and deoxyribounucleosides, *Life Sci.*, 38, 1451–1457).

FOOD RESTRICTION AND CANCER PREVENTION

It has been know for 45 years that reducing the food intake of laboratory mice inhibits the development of a broad spectrum of spontaneous and chemically induced tumors (Tannenbaum, A. (1940); The Initiation and Growth of Tumors. Introduction. I. Effects of Underfeeding, *Am. J. Cancer*, 38, 335–350), but the mechanism of this effect is not clear. It appears that food restriction of mice for two weeks inhibits both the binding of $^3$H-DMBA to skin DNA as well as the TPA stimulation of epidermal $^3$H-thymidine incorporation (Tables 4 and 6) to a degree comparable to that observed with an application of 400 ug of DHEA. Both of these effects of food restriction very likely result from a depression in G6PDH activity (Table 7). Thus inhibition of G6PDH activity may be an important component in the cancer preventive effects of both food restriction and DHEA treatment.

Administration of DHEA at a daily dose of approximately 400 mg/kg in long-term experiments has been shown to inhibit the development of breast, lung, and colon tumors. This dose of DHEA, when administered repeatedly over a period of a few weeks, also produces an anti-weight effect. However, a single administration of DHEA at 400 mg/kg to mice does not inhibit $^3$H-DMBA binding to skin DNA and does not inhibit the TPA stimulation in epidermal $^3$H-thymidine incorporation to a degree comparable to that produced by either food restriction or an topical application of 400 ug of DHEA. (Table 9 vs Table 5 and Table 6). However, treatment of mice for four weeks with 400 mg/kg of DHEA does inhibit $^3$H-DMBA binding to skin DNA, but this regimen of DHEA treatment also produces an anti-weight effect, which is due to both a reduction in food intake and to a decrease in the efficiency of food utilization. Thus the cancer preventive the cancer preventive effect of DHEA may result indirectly from its anti-weight action rather than from a direct effect of DHEA or target cells.

However, compounds 8353, 8354, A and B when administered orally to mice, inhibit $^3$H-DMBA binding to skin DNA and TPA stimulation in $^3$H-thymidine incorporation (Tables 3, 8 and 9) to a degree comparable to that produced by food restriction at doses well below 400 mg/kg, whereas DHEA is inactive. At these dosages the new compounds do not produce an anti-weight effect with the possible exception of 8354 which appears to be several times more active than DHEA as an anti-obesity agent. Therefore, the cancer preventive activities of the present compounds are more potent than the cancer preventive activity of DHEA, and in addition, the cancer preventive activity of the present new steroids has been dissociated from the anti- obesity effect.

TABLE 3

EFFECT OF ORALLY ADMINISTERED COMPOUNDS A AND B ON TPA STIMULATION OF $^3$H-THYMIDINE INCORPORATION IN MOUSE EPIDERMIS

| TREATMENT | SPECIFIC ACTIVITY (cpm/ug DNA) |
|---|---|
| No steroid | 70.2 ± 2.3 (n = 2) |
| No steroid plus TPA | 154 ± 16 (n = 2) |
| TPA plus cpd A (100 mg/kg) | 8.1 ± 4.1 (n = 3) |
| TPA plus cpd A (50 mg/kg) | 35.2 ± 1.8 (n = 3) |
| TPA plus cpd A (25 mg/kg) | 77.4 ± 10.4 (n = 3) |
| TPA plus cpd B (100 mg/kg) | 7.2 ± 3.8 (n = 3) |
| TPA plus cpd B (50 mg/kg) | 25.6 ± 4.0 (n = 3) |
| TPA plus cpd B (25 mg/kg) | 66.1 ± 9.8 (n = 3) |

Male ICR mice were orally intubated with steroid suspended in sesame oil (0.5 ml/mouse) at the indicated dose. Mice not receiving steroid were given sesame oil alone. One hour later mice received topical application of TPA and 20 hours later the rate of $^3$H-thymidine incorporation into the epidermis was determined as described in Pashko, L. L., Schwartz, A. G., Abou-Gharbia, M., and Swern, D. (1981), Inhibition of DNA synthesis in mouse epidermis and breast epithelium by dehydroepiandrosterone and related steroids, *Carcinogenesis*, 2, 717–721.

TABLE 4

EFFECT OF STEROID TREATMENT OR TWO WEEKS OF FOOD RESTRICTION ON ($^3$H) DMBA BINDING TO SKIN DNA

| TREATMENT | SPECIFIC ACTIVITY (cpm/ug DNA) |
|---|---|
| Ad libitum fed | 116 ± 5.2 |
| Ad libitum fed plus DHEA | 66 ± 13 |
| Ad libitum fed plus testosterone | 164 ± 8.4 |
| Food restricted (two weeks) | 57 ± 14 |

Binding of [$^3$H]DMBA to mouse skin DNA was determined as described in Pashko, L. L., and Schwartz, A. G. (1983), Effect of food restriction, dehydroepiandrosterone, or obesity on the binding of $^3$H-7,12-dimethylbenz(a)anthracene to mouse skin DNA, *J. Gerontol.*, 38, 8–12. Values are mean±SD for 3 individual determinations, with pooled tissue from 2 mice used for each determination. DHEA or testosterone (400 ug in 0.2 ml acetone) was applied to the skin one hour before [$^3$H]DMBA. The mean weight of the food restricted mice was 18.5±1.0 gm, n=6, of the ad libitum fed, 27.4±1.0 gm, n=6, of the ad libitum fed treated with DHEA, 28.2±0.9 gm, n=6, and of the ad libitum fed treated with testosterone, 28.3±0.9 gm, n=6, following two weeks of feeding. The average food consumed was, in gm/mouse/day, 2.2, 3.8, 3.8 and 4.0 for the food restricted, ad libitum fed, ad libitum fed plus DHEA, and ad libitum fed plus testosterone groups, respectively.

\*Significantly less than ad libitum fed mice, p<0.01;
\*\*Significantly greater than ad libitum fed mice, p<0.01.

TABLE 5
INHIBITION OF TPA STIMULATION OF $^3$H-THYMIDINE INCORPORATION IN EPIDERMIS BY DHEA

| TREATMENT | SPECIFIC ACTIVITY (cpm/ug DNA) |
|---|---|
| No steroid | 66 ± 1.8 |
| No steroid plus TPA | 174 ± 35 |
| TPA plus DHEA (100 ug) | 52 ± 5.8 |
| TPA plus DHEA (400 ug) | 22 ± 6.5 |
| TPA plus testosterone (100 ug) | 128 ± 13 |
| TPA plus testosterone (400 ug) | 142 ± 5.9 |

Incorporation of $^3$H-thymidine into A/J mouse epidermal DNA was determined as described in Pashko, L. L., Schwartz, A. G., Abou-Gharbia, M. and Swern, D. (1981), Inhibition of DNA synthesis in mouse epidermis and breast epithelium by dehydroepiandrosterone and related steroids, *Carcinogenesis*, 2, 717–721. Values are mean±SD for 3 separately treated mice in each group 20 hours after TPA application. DHEA or testosterone was added topically in 0.2 ml acetone one hour before TPA addition.

TABLE 6
EFFECT OF TWO WEEKS OF FOOD RESTRICTION ON TPA STIMULATION OF EPIDERMAL $^3$H-THYMIDINE INCORPORATION

| TREATMENT | SPECIFIC ACTIVITY (cpm/ug DNA) |
|---|---|
| *Ad libitum* fed | 54 ± 0.8 |
| *Ad libitum* fed plus TPA | 193 ± 25 |
| Food restricted (two weeks) plus TPA | 34 ± 6.8 |

Incorporation of $^3$H-thymidine into A/J mouse epidermal DNA was determined as described in Table 5. Values are mean±SD for 3 separately treated mice in each group. The means weight of the food restricted mice was 18.3±0.6 gm n=3, and of the ad libitum fed was 26.7±1.4, n=6, following two weeks of feeding. The average food consumed was 2.4 gm/mouse/day for food restricted and 4.9 gm/mouse/day for ad libitum fed mice.

TABLE 7
EFFECT OF TWO WEEKS OF FOOD RESTRICTION ON EPIDERMAL G6PDH ACTIVITY

| TREATMENT | SPECIFIC ACTIVITY (nmoles NADPH/mg protein min) |
|---|---|
| *Ad libitum* fed | 43.4 ± 6.0 |
| Food restricted (two weeks) | 18.1 ± 5.1 |

Epidermal G6PDH activity was determined as described in Ziboh, V. A., Dreize, M. A., and Hsia, S. L. (1970), Inhibition of lipid synthesis and glucose-6-phosphate dehydrogenase in rat skin by dehydroepiandrosterone, *J. Lipid Res.*, 11, 346–351 and Glock, G. E. and McClean, P. (1953). Further studies on the properties of glucose-6-phosphate dehydrogenase and 6-phosphogluconate dehydrogenase of rat liver, *Biochem. J.*, 55, 400–408. Values are mean±SD for three separate determinations, with pooled epidermal tissue from 4 mice used for each determination. The mean weight of the food restricted mice was 18.4±0.8 gm, n=12. The average food consumed was 2.4 gm/mouse/day for food restricted and 3.9 gm/mouse/day for the ad libitum fed mice.

TABLE 8
EFFECT OF ORALLY ADMINISTERED 8353 ON TPA STIMULATION OF $^3$H-THYMIDINE INCORPORATION IN MOUSE EPIDERMIS

| TREATMENT | SPECIFIC ACTIVITY (cpm/ug DNA) |
|---|---|
| TPA plus 8353 (200 mg/kg, p.o.) | 14.3 ± 1.7 (n = 3) |
| TPA plus 8353 (150 mg/kg, p.o.) | 14.0 ± 1.1 (n = 3) |
| TPA plus 8353 (75 mg/kg, p.o.) | 15.9 ± 2.4 (n = 3) |

Experimental conditions are the same as in Table 3.

TABLE 9
EFFECT OF ORALLY ADMINISTERED DHEA OR 8354 ON TPA STIMULATION OF $^3$H-THYMIDINE INCORPORATION IN MOUSE EPIDERMIS

| TREATMENT | SPECIFIC ACTIVITY (cpm/ug DNA) |
|---|---|
| No steroid | 55.1 ± 1.6 (n = 3) |
| No steroid plus TPA | 118 ± 10.5 (n = 3) |
| TPA plus DHEA (400 mg/kg) | 50.9 ± 3.2 (n = 3) |
| TPA plus 8354 (100 mg/kg) | 15.0 ± 6.3 (n = 3) |
| TPA plus 8354 (50 mg/kg) | 36.2 ± 1.4 (n = 3) |
| TPA plus 8354 (25 mg/kg) | 47.9 ± 2.0 (n = 3) |

Experimental conditions are the same as in Table 3.

Male A/J (5 weeks old) mice were obtained from the Jackson Laboratory and were housed in polycarbonate cages (6 mice/cage) in animal quarters maintained at 24°±1° C. with 12 hours of light and 12 hours of darkness each day. One week after arrival, the mice were placed on a diet containing either DHEA, 8353, or without steroid. Animals were weighed weekly.

TABLE 10
ANTI-OBESITY ACTION OF 8353 AND DHEA

| | mean weekly weight in grams ± S.D. (n = 6) | | |
|---|---|---|---|
| Week | Control (no steroid) | DHEA (0.45%) | 8353 (0.45%) |
| 0 | 23 ± 1.5 | 23.0 ± 1.5 | 23.3 ± 1.6 |
| 1 | 25.0 ± 1.6 | 22.8 ± 1.5 | 21.1 ± 1.4 |
| 2 | 27.0 ± 1.6 | 19.0 ± 1.5 | 21.9 ± 1.0 |
| 3 | 27.3 ± 1.6 | 21.5 ± 1.1 | 23.6 ± 1.5 |
| 4 | 27.5 ± 1.9 | 21.4 ± 1.2 | 23.5 ± 1.5 |

Female Balb/c (8 weeks old) mice were obtained from the Jackson Laboratory and were housed in polycarbonate cages (6 mice/cage) in animals quarters maintained at 24°±1° C. with 12 hours of light and 12 hours of darkness each day. One week after arrival, the mice were placed on a diet containing either DHEA, 8354, or without steroid. Animals were weighed weekly.

TABLE 10A

| | mean weekly weight in grams ± S.D. (n = 6) | | |
|---|---|---|---|
| Week | Control (no steroid) | DHEA (0.25%) | 8354 (0.25%) |
| 0 | 17.5 ± 1.4 | 17.5 ± 1.5 | 17.4 ± 0.6 |
| 1 | 19.9 ± 1.2 | 20.0 ± 0.9 | 16.9 ± 1.0 |
| 2 | 20.6 ± 1.0 | 20.6 ± 0.9 | 17.8 ± 0.8 |
| 3 | 21.8 ± 0.8 | 21.3 ± 1.3 | 18.0 ± 1.3 |

1. INDUCTION OF HEPATOMEGACY AND LIVER CATALASE BY DHEA: LACK OF EFFECT FOLLOWING TREATMENT WITH 8354 or CMPD. B

In addition to lacking the estrogenic and androgenic side-effects of DHEA, compounds 8354, A and B have been found to lack another side-effect produced by DHEA treatment. DHEA, when orally administered to mice and rats over a dose range of 0.2% to 0.6%, produces liver enlargement. A similar enlargement is seen following treatment with the drug clofibrate and is believed to be due to peroxisome proliferation in the liver. Peroximsome proliferation results in increased levels of catalase in the liver, and in mice and rats this condition can enhance liver tumor formation. We have found that after three weeks of oral treatment of mice (0.25% of diet) with either DHEA, clofibrate, 8354, A or B, both DHEA and clofibrate increased liver weight and stimulated catalase activity, whereas compounds 8354, A and B had no effect on liver weight or catalase activity.

Enlargement of liver appears to be a characteristic response in laboratory animals and in man exposed to a variety of drugs or xenobiotic agents (Reddy, J. K. et al., Hepatic and Renal Effects of Peroxisome Proliferators: Biological Implications, *Annals N. Y. Acad. Sci.* (1982), 386 81-110). Two types of hepatomegaly are currently recognized: 1. Those occurring in response to drugs (phenobarbital, DDT, etc.) which stimulate proliferation of smooth endoplasmic reticulum in liver cells and induce microsomal drug metabolizing enzymes, and 2. Those occurring in response to administration of peroxisome proliferators. Typical peroxisome proliferators are various hypolipidemic drugs, such as clofibrate, and the plasticizer, di(2-ethylhexyl)phthalate. Sustained treatment of mice or rats with peroxisome proliferators can lead to hepatocellular carcinoma.

Our laboratory and others (Cleary, M. P., Fox, N., Lazin, B., and Billheimer, J. T., *Nutr. Res.* 5, 1247-1257, 1985, A Comparison of the Effects of Dehydroepiandrosterone Treatment to Ad Libitum and Pair Feeding in the Obese Zucker Rat) have found that treatment of rats or mice with therapeutic doses of DHEA (0.2% to 0.6% in the diet) produces hepatomegaly. Moore, et al. (*Carcinogenesis* 7, 311-316, 1986, Modifying Influence of Dehydroepiandrosterone on the Development of Dihydroxy-di-n-propylnitrosamine-initiated Lesions in the Thyroid, Lung, and Liver of F344 Rats) have found that treatment of rats with 0.6% DHEA for 20-22 weeks following 4 injections of the carcinogen dihydroxy-di-n-propylnitrosamine inhibited the formation of enzyme-positive premalignant foci in the liver. However, they also found that DHEA promoted the development of liver basophilic lesions which were enzyme-negative. These latter lesions were also produced by treatment with diethylhexylphthalate, and the authors suggested that DHEA may be active as a peroxisome proliferator.

Peroxisomes contain high levels of catalase, and increase in the specific activity of liver catalase is characteristic of the hepatomegaly seen with treatment with peroxisome proliferators.

We have found that treatment of mice with DHEA or clofibrate (0.25%) for three weeks causes both hepatomegaly and a threefold increase in liver catalase specific activity. These results are consistent with the findings of Moore, et al. and indicate that DHEA is a peroxisome proliferator. However, compounds 8354, A and B neither increased liver weight nor stimulated catalase activity (Table 11). This surprising finding with 8354 and B indicates that a potentially serious side-effect of DHEA treatment has apparently been eliminated.

TABLE 11

EFFECT OF STEROID OR CLOFIBRATE TREATMENT ON LIVER WEIGHT AND CATALASE ACTIVITY

| TREATMENT | LIVER WEIGHT (gm/gm body weight) | CATALASE ACTIVITY (Units per mg protein) |
| --- | --- | --- |
| DHEA (0.25%) | 0.074 ± 0.005* | 97.8 ± 24* |
| 8354 (0.25%) | 0.066 ± 0.005 | 29.2 ± 2.6 |
| A (0.25%) | 0.058 ± 0.004 | 42.3 ± 7.2 |
| B (0.25%) | 0.061 ± 0.002 | 32.2 ± 6.0 |
| Clofibrate (0.25%) | 0.084 ± 0.006** | 92.1 ± 8.9*** |
| Control | 0.057 ± 0.006 | 31.1 ± 6.7 |

Values are the means ± SD for three separate determinations.
*Significantly greater than control value, $p < 0.05$;
**Significantly greater than control value, $p < 0.002$;
***Significantly greater than control value, $p < 0.001$.

Female Balb/c mice were housed in polycarbonate cages (6/mice/cage) in animal quarters maintained at 24°±1° C. with 12 hours of light and 12 hours of dark each day. The mice were placed on a diet containing either DHEA, 8354, A, B, clofibrate or with no addition. Three weeks later the mice were killed, the livers were perfused with cold saline, weighed, and 5% liver homogenates were prepared for the determination of catalase activity by the spectrophotometric method of Luck (H. Luck, in *Method in Enzyme Analysis*, H. U. Bergmeyer, Ed. (Verlag Chemie, Weinheim/Bergstrasse, Germany, 1965)). Total protein was measured by the method of Lowry, et al. (O. H. Lowry, N. J. Rosebrough, A. L. Farr, R. J. Randall, *J. Biol. Chem.*, 193, 265 (1951)).

Anti-Antoimmune Activity

New Zealand Black (NZB) mice develop a progressive autoimmune, Coomb's positive hemolytic anemia with age. It has been previously found that long term treatment of NZB mice with DHEA significantly inhibits the rate of development of the autoimmune anemia. Tannen, R. H., Schwartz, A. G., 1982 Reduced Weight Gain and Delay of Coomb's Positive Hemolytic Anemia in NZB Mice Treated with Dehydroiepiandrosterone (DHEA), *Fed. Proc.*, 41, 463 (Abstract). Lucas et al. in *J. Clin. Invest.*, 75, 2091-2093 (1985) have shown that the oral administration of dehydroisandrosterane prolonged the survival of New Zealand Black/New Zealand White F, hybrid mice against murine lupus erythematosus. In other studies reported herein, we have determined that the compounds of the present invention have retained physiological action, such as cancer preventive action, of DHEA without any apparent estrogenic effect. There is a reasonable probability that such steroids will also retain the anti-autoimmune activity of DHEA.

The compounds, i.e. therapeutic agents of this invention, may be administered alone or in combination with pharmaceutically-acceptable carriers, the proportion of which is determined by the solubility and chemical nature of the compound, chosen route of administration and standard pharmaceutical practice. For example, they may be administered orally in the form of tablets, pills or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

When given orally, the therapeutic doses of the compounds of the present invention are generally in the range of from about 4 to about 450 mg/kg/day depending upon the particular mammalian host and the particular effect desired, e.g. cancer preventive, anti-obesity, anti-diabetes, etc., when given parenterally, the compounds are administered generally in dosages of, for example, 0.5 to about 15 mg/kg/day, also depending upon the host and effect desired.

Obviously, other modifications and variations of the present invention are possible in light of the above teachings. It is, therefore, to be understood that changes may be made in the particular embodiments of this invention which are within the full intended scope of the invention as defined by the appended claims.

What is claimed is:

1. A process for the prophylaxis of obesity in an animal, said process comprising administering to said animal an anti-obesity effective amount of a compound having the following formula:

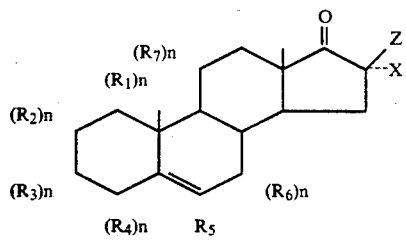

wherein
$R_1$, $R_2$, $R_4$, $R_5$, $R_6$, and $R_7$, are each independently hydrogen or lower alkyl;
$R_3$ is hydrogen;
X is halogen, hydroxy, hydrogen, lower alkyl or lower alkoxy;
Z is lower alkyl or hydrogen; and n is 1 or 2; with the proviso that at least one of X and Z is other than hydrogen.

2. The process according to claim 1 wherein alkyl contains 1-5 carbon atoms.

3. The process according to claim 2 wherein alkyl is methyl.

4. The process according to claim 1 wherein X is fluoro.

5. The process according to claim 1 wherein the compound has the formula:

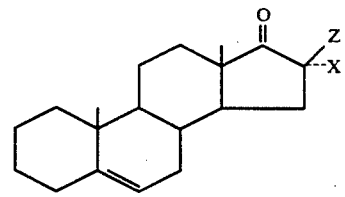

wherein
X is halogen, hydroxy, hydrogen, or lower alkyl; and
Z is lower alkyl or hydrogen; with the proviso that at least one of X and Z is other than hydrogen.

6. The process according to claim 5 wherein alkyl contains 1-3 carbon atoms.

7. The process according to claim 6 wherein alkyl is methyl.

8. The process according to claim 5 wherein X is fluoro.

9. The process according to claim 1 wherein the compound is:

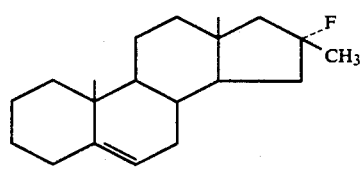

10. The process according to claim 1 wherein the compound is:

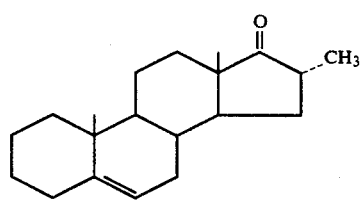

11. A process for the prophylaxis of obesity in an animal which comprises administering to said animal an anti-obesity effective amount of a compound having the formula:

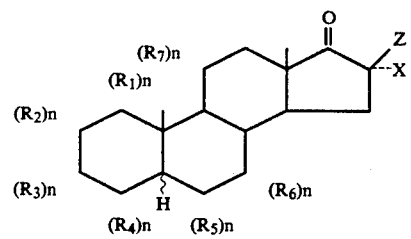

wherein
$R_1$, $R_2$, $R_4$, $R_5$, $R_6$, and $R_7$, are each independently hydrogen or lower alkyl;
$R_3$ is hydrogen;
X is chloro, fluoro, hydroxy, hydrogen, lower alkyl, or lower alkoxy;
Z is lower alkyl or hydrogen; and n is 1 or 2; with the proviso that at least one of X and Z is other than hydrogen.

12. The process according to claim 11 wherein alkyl is lower alkyl having 1-5 carbon atoms.

13. The process according to claim 12 wherein alkyl is methyl.

14. The process according to claim 11 wherein X is fluoro.

15. The process according to claim 11 wherein the compound has the formula:

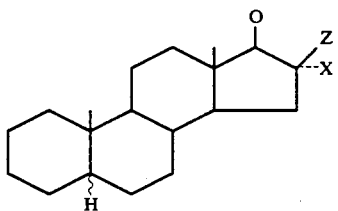

wherein X is fluoro, chloro, hydroxy, hydrogen, or lower alkyl and

Z is lower alkyl or hydrogen with the proviso that at least one of X and Z is other than hydrogen.

16. The process according to claim 15 wherein the compound is:

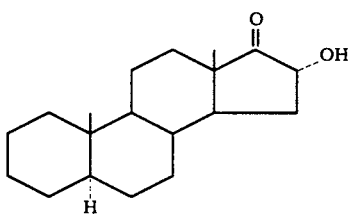

17. The process according to claim 15 wherein the compound is:

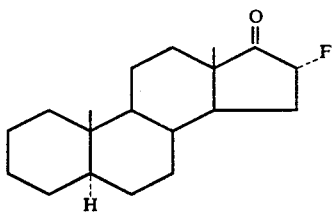

18. The process according to claim 1, wherein the compound has the formula:

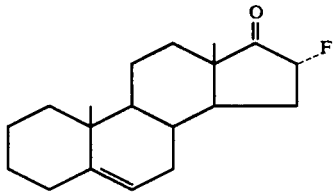

19. The process according to claim 1 wherein the compound has the formula:

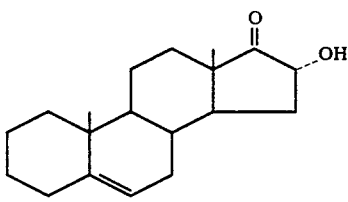

* * * * *